United States Patent [19]
Hartlaub et al.

[11] Patent Number: 6,070,102
[45] Date of Patent: May 30, 2000

[54] AUDIBLE SOUND CONFIRMATION OF PROGRAMMING AN IMPLANTABLE MEDICAL DEVICE

[75] Inventors: Jerome T. Hartlaub, New Brighton; David L. Thompson, Fridley; Daniel R. Greeninger, Coon Rapids, all of Minn.

[73] Assignee: Medtronic, Inc., Minneapolis, Minn.

[21] Appl. No.: 09/069,516

[22] Filed: Apr. 29, 1998

[51] Int. Cl.⁷ ..................................................... A61N 1/362
[52] U.S. Cl. ................................................. 607/31; 607/9
[58] Field of Search ........................................... 607/9, 31

[56] References Cited

U.S. PATENT DOCUMENTS

| | | |
|---|---|---|
| H1347 | 8/1994 | Greeninger et al. ....................... 607/30 |
| 3,672,352 | 6/1972 | Summers . |
| 4,041,954 | 8/1977 | Ohara . |
| 4,102,346 | 7/1978 | Fulker . |
| 4,140,131 | 2/1979 | Dutcher et al. . |
| 4,210,149 | 7/1980 | Heilman et al. . |
| 4,226,245 | 10/1980 | Bennett, Jr. . |
| 4,273,132 | 6/1981 | Hartlaub et al. . |
| 4,313,079 | 1/1982 | Lee . |
| 4,345,603 | 8/1982 | Schulman . |
| 4,445,512 | 5/1984 | Krupka et al. . |
| 4,481,950 | 11/1984 | Duggan . |
| 4,488,555 | 12/1984 | Imran . |
| 4,520,825 | 6/1985 | Thompson et al. . |
| 4,619,653 | 10/1986 | Fischell . |
| 4,832,033 | 5/1989 | Maher et al. . |
| 4,890,259 | 12/1989 | Simko . |
| 5,076,272 | 12/1991 | Ferek-Petric . |
| 5,080,096 | 1/1992 | Hooper et al. . |
| 5,285,792 | 2/1994 | Sjoquist et al. . |
| 5,292,342 | 3/1994 | Nelson et al. . |
| 5,391,188 | 2/1995 | Nelson et al. . |
| 5,433,736 | 7/1995 | Nilsson ..................................... 607/59 |
| 5,438,990 | 8/1995 | Wahlstrand et al. . |
| 5,443,486 | 8/1995 | Hrdlicka et al. . |
| 5,535,752 | 7/1996 | Halperin et al. . |
| 5,564,434 | 10/1996 | Halperin et al. . |
| 5,573,506 | 11/1996 | Vasko . |
| 5,620,475 | 4/1997 | Magnusson . |
| 5,653,735 | 8/1997 | Chen et al. ................................. 607/9 |
| 5,745,019 | 4/1998 | Renger . |

OTHER PUBLICATIONS

"ISD33000 Series Single–Chip Voice Record/Playback Devices" Product Data Sheets for Information Storage Devices, Inc., pp. 1–107–1–127. (undated).
"Champion Pacing System" Product Information Manual, Model 7302, Medtronic, Inc., Dec. 1996.
"Champion Pacing System" Pacemaker Follow–Up and Programming Guide, Medtronic, Inc., Jan. 1997.
PCT International Search Report, P–7031.02, PCT/US 99/08824, Apr. 21, 1999, Medtronic, Inc.

*Primary Examiner*—William E. Kamm
*Assistant Examiner*—Carl H. Layno
*Attorney, Agent, or Firm*—Thomas F. Woods; Girma Wolde-Michael; Harold R. Patton

[57] ABSTRACT

Methods and apparatus for confirming programming of implantable medical device (IMD) operating parameter values and operating modes by emission of audible sounds by the IMD are disclosed. The IMD includes an audio transducer that emits audible sounds including voiced statements or musical tones stored in analog memory correlated to a programming or interrogation operating algorithm or to a warning trigger event. The audible sounds can comprise the sole uplink transmission or may augment the contemporaneous uplink RF transmission of stored data, and/or programmed operating modes and parameters and/or device operations and states in an interrogation or during programming. To conserve energy, the audible sounds accompanying interrogation and programming of the IMD are at a low volume that preferably cannot be heard without use of an external audio amplifier or stethoscope. Voiced statements warning of battery energy depletion or imminent delivery of a therapy are emitted at a higher volume that is sufficient to be heard by the patient, so that the patient can take appropriate action. The volume of audible sounds confirming programmed changes made by a patient using a limited function programmer or magnet is also increased so that the patient can hear them.

29 Claims, 14 Drawing Sheets

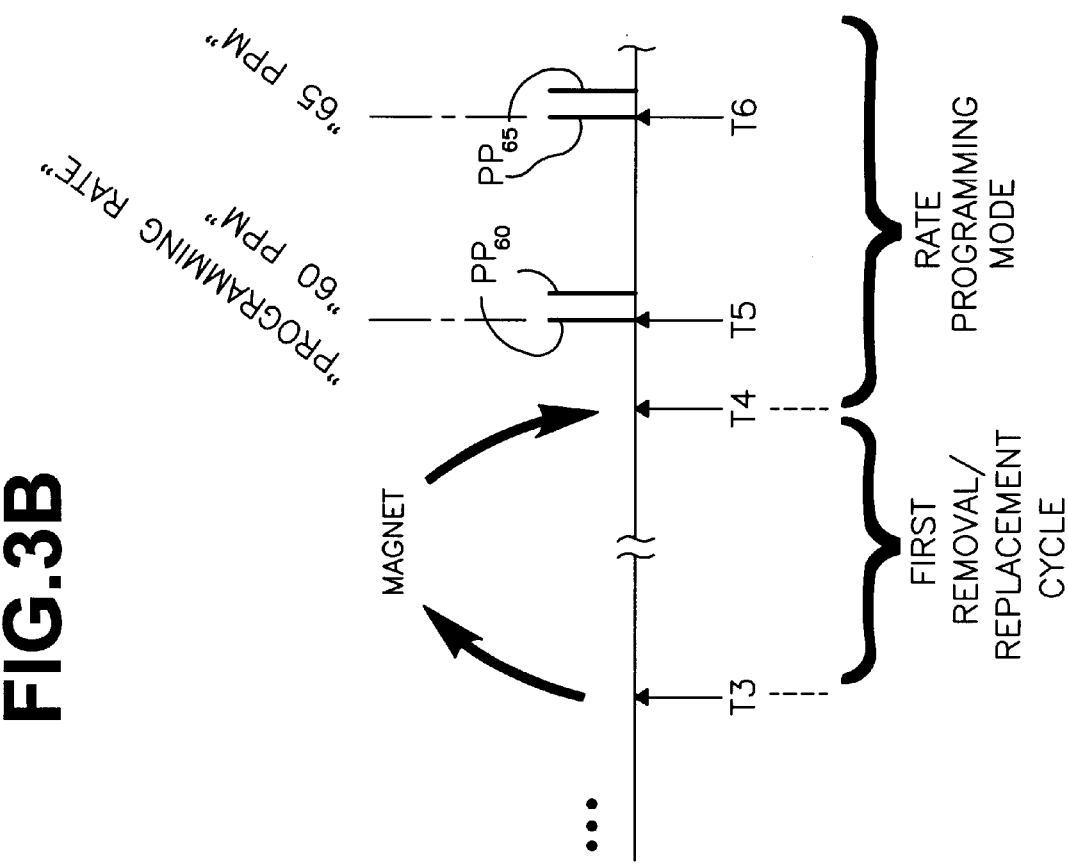

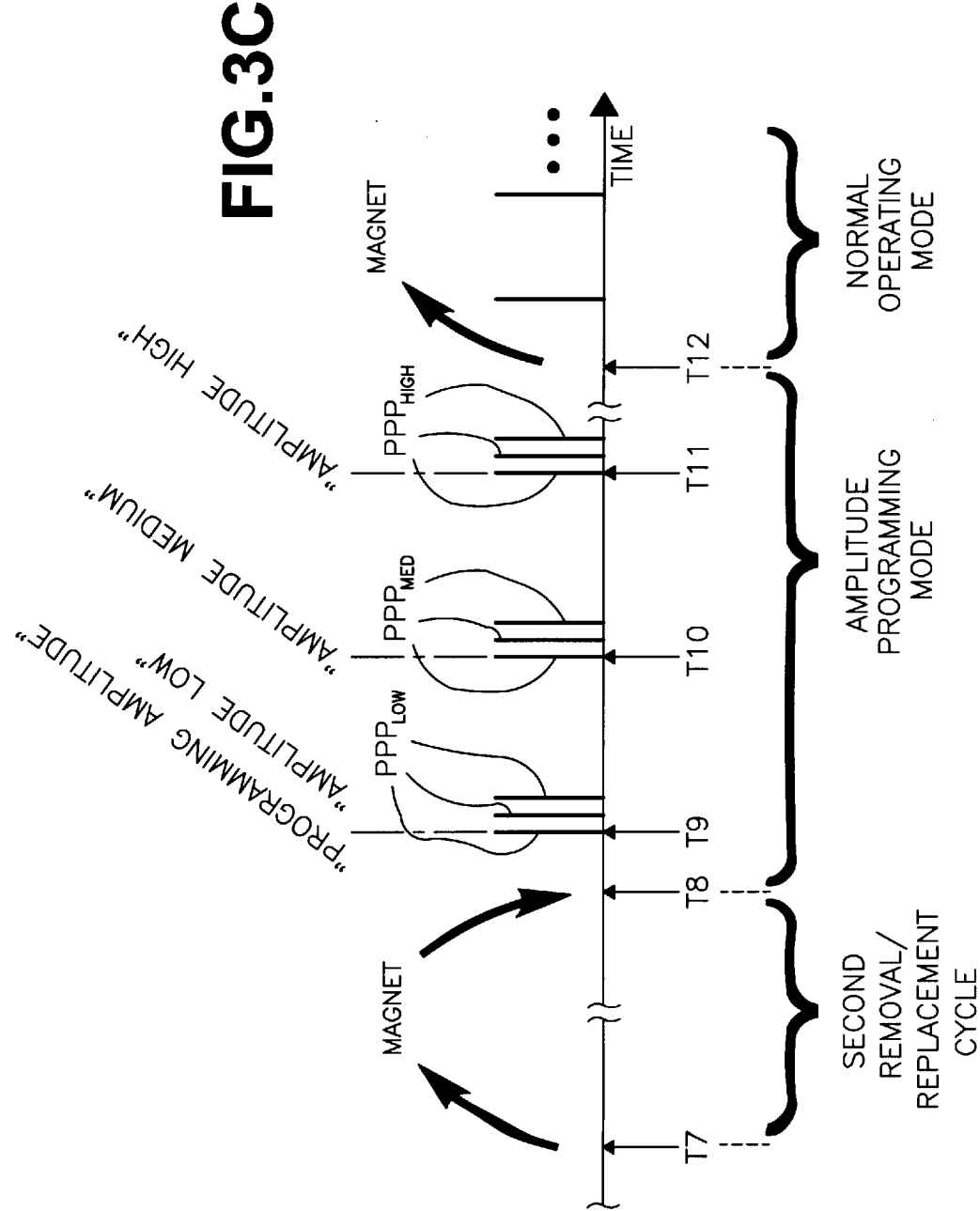

| Address (hex) | Phrase stored at Address |
|---|---|
| 00 | 50 ppm |
| 01 | 55 ppm |
| 02 | 60 ppm |
| 03 | 65 ppm |
| 04 | 70 ppm |
| 05 | 75 ppm |
| 06 | 80 ppm |
| 07 | 85 ppm |
| 08 | 90 ppm |
| 09 | 95 ppm |
| 0A | 100 ppm |
| 0B | 0.1 Milliseconds |
| 0C | 0.2 Milliseconds |
| 0D | 0.3 Milliseconds |
| 0E | 0.4 Milliseconds |
| 0F | 0.5 Milliseconds |
| 10 | 0.6 Milliseconds |
| 11 | 0.7 Milliseconds |
| 12 | 0.8 Milliseconds |
| 13 | 0.9 Milliseconds |
| 14 | 1.0 Milliseconds |
| 15 | Medtronic Model XYZ Serial Number 1234 |
| 16 | Amplitude High |
| 17 | Amplitude Low |
| 18 | Battery ERI |
| 19 | Battery OK |
| 1A | Pace |
| 1B | Sense |
| 1C | Programming |
| 1D | Rate |
| 1E | Width |
| 1F | Amplitude |

| Address (hex) | Phrase stored at Address |
|---|---|
| 00 | Data start or ♪♪♪ |
| 01 | Infusion rate three hundred milliliters per day |
| 02 | Infusion rate one tenth milliliter per day |
| 03 | Infusion rate three tenths milliliter per day |
| 04 | Infusion rate one milliliter per day |
| 05 | Infusion rate three milliliters per day |
| 06 | Over 30 days drug remaining |
| 07 | Over 20 days drug remaining |
| 08 | Over 10 days drug remaining |
| 09 | Over 5 days drug remaining |
| 0A | Less than 2 days drug remaining or ♪♪♪ |
| 0B | Greater than 60 days battery remaining |
| 0C | Less than 60 days battery remaining or ♪♪♪ |
| 0D | End data |
| 0E | Rate increasing or ♪♪♪ |
| 0F | Rate decreasing or ♪♪♪ |
| 10 | Data end or ♪♪♪ |
| | |
| | |

| Address (hex) | Phrase stored at Address |
|---|---|
| 00 | 2 pps |
| 01 | 10 pps |
| 02 | 20 pps |
| 03 | 40 pps |
| 04 | 80 pps |
| 05 | 100 pps |
| 06 | 130 pps |
| 07 | 60 microseconds |
| 08 | 120 microseconds |
| 09 | 180 microseconds |
| 0A | 240 microseconds |
| 0B | 300 microseconds |
| 0C | 360 microseconds |
| 0D | 420 microseconds |
| 0E | 450 microseconds |
| 0F | 0 volts |
| 10 | 1 volt |
| 11 | 2 volts |
| 12 | 4 volts |
| 13 | 7 volts |
| 14 | 10 volts |
| 15 | Medtronic Model XYZ Serial Number 1234 |
| 16 | Battery ERI |
| 17 | Battery OK |
| 18 | Cycle ON |
| 19 | Cycle OFF |
| 1A | Electrode 1 |
| 1B | Electrode 2 |
| 1C | Electrode 3 |
| 1D | Electrode 4 |
| 1E | increasing or ♪♪♪ |
| 1F | decreasing or ♪♪♪ |

FIG.12

AUDIBLE SOUND CONFIRMATION OF PROGRAMMING AN IMPLANTABLE MEDICAL DEVICE

CROSS-REFERENCE TO RELATED APPLICATION

Reference is hereby made to commonly assigned, co-pending U.S. patent application Ser. Nos. 09/069,284 filed on even date herewith for INTERROGATION OF AN IMPLANTABLE MEDICAL DEVICE USING AUDIBLE SOUND COMMUNICATION in the names of D. Greeninger et al. 09/069,559 and filed on even date herewith for AUDIBLE SOUND COMMUNICATION FROM AN IMPLANTABLE MEDICAL DEVICE in the names of D. Greeninger et al.

FIELD OF THE INVENTION

The present invention relates generally to improved methods and apparatus for providing uplink transmission of implantable medical device (IMD) information by audible sounds emitted by the IMD during programming the IMD.

BACKGROUND OF THE INVENTION

Early IMDs such as implantable cardiac pacemakers were designed to operate in a typically single operating mode governed by fixed operating parameters without any ability to change the operating mode or otherwise communicate percutaneously with external equipment. In time, it became apparent that it would be clinically desirable to vary certain of the operating parameters and/or modes of operation. An initial approach employed with implanted cardiac pacemakers involved use of miniature rheostats that could be directly accessed by a needle-like tool inserted through the patient's skin to adjust a resistance in the pacing rate or pulse width setting circuit. Later, miniaturized reed switches were incorporated into the pacing rate or pulse width circuits that responded to magnetic fields applied through the skin by an external magnet placed over the implant site. The pulse width, pacing rate and a limited number of pacing modes could be adjusted in this manner.

It was also realized that the operation of an implantable cardiac pacemaker could be observed, for example, by use of a standard EKG machine and timing of intervals between pacing pulse spikes in the ECG tracing recorded from skin electrodes on the patient. The applied magnet was used to close a reed switch to change the pacing mode to an asynchronous pacing mode and to encode the fixed pacing rate or pulse amplitude or width to a value reflecting a current operating parameter. One use of this technique was to monitor impending battery depletion through observation of a change in the pacing rate from a preset or programmed pacing rate in response to a battery voltage drop, as described, for example, in U.S. Pat. No. 4,445,512. This approach could only provide a low bandpass data channel, of course, to avoid interfering with the primary function of pacing the patient's heart when necessary.

As digital circuit technology advanced, it was recognized that control of operating modes and parameters of implanted medical devices could be realized in digital or binary circuits employing memorized control states or operating parameter values. In order to change an operating mode or parameter value, "programmers" were developed based on radio frequency (RF) downlink data communication from an external programmer transceiver to a telemetry transceiver and memory incorporated within the IMD.

Through the use of such telemetry systems, it became possible to provide uplink data telemetry to transmit the contents of a register or memory within the IMD to the telemetry receiver within the programmer employing the same RF transmission capabilities. Today, both analog and digital data can be transmitted by uplink RF telemetry from the implanted medical device to the external programmer. In the context of implantable cardiac pacemakers, the analog data typically includes battery status, sampled intracardiac electrocardiogram amplitude values, sensor output signals, pacing pulse amplitude, energy, and pulse width, and pacing lead impedance. The digital data typically includes statistics related to performance, event markers, current values of programmable parameters, implant data, and patient and IMD identification codes.

The telemetry transmission system that evolved into current common use relies upon the generation of low amplitude magnetic fields by current oscillating in an LC circuit of an RF telemetry antenna in a transmitting mode and the sensing of currents induced a closely spaced RF telemetry antenna in a receiving mode. Short duration bursts of the carrier frequency are transmitted in a variety of telemetry transmission formats. In the MEDTRONIC® product line, the RF carrier frequency is set at 175 kHz, and the RF telemetry antenna of the IMD is typically coiled wire wound about a ferrite core that is located within the hermetically sealed enclosure. The RF telemetry antenna of the external programmer is contained in a programming head together with a permanent magnet that can be placed on the patient's skin over the IMD to establish a magnetic field within the hermetically sealed enclosure of the IMD.

In an uplink telemetry transmission from an implanted medical device, it is desirable to limit the current drain from the implanted battery as much as possible simply to prolong device longevity. However, as device operating and monitoring capabilities multiply, it is desirable to be able to transmit out ever increasing volumes of data in real time or in as short a transmission time as possible with high reliability and immunity to spurious noise. As a result of these considerations, many RF telemetry transmission data encoding schemes have been proposed or currently are used that attempt to increase the data transmission rate.

At present, a wide variety of IMDs are commercially released or proposed for clinical implantation that are programmable in a variety of operating modes and are interrogable using RF telemetry transmissions. Such medical devices include implantable cardiac pacemakers, cardioverter/defibrillators, pacemaker/cardioverter/defibrillators, drug delivery systems, cardiomyostimulators, cardiac and other physiologic monitors, electrical stimulators including nerve and muscle stimulators, deep brain stimulators, and cochlear implants, and heart assist devices or pumps, etc. As the technology advances, IMDs become ever more complex in possible programmable operating modes, menus of available operating parameters, and capabilities of monitoring increasing varieties of physiologic conditions and electrical signals. These complexities place ever increasing demands on the programming and interrogation system and the medical care providers using them.

In our Statutory Invention Registration H1347, we disclose an improvement to programmers of this type adding audio voiced statements that accompany their operations to assist the medical care provider using them. For example, we propose adding voiced statements that track interactive operation of a programmer and implanted medical device during programming and patient follow-up sessions that can be heard by the medical care provider using the programmer.

Such voiced statements would augment or replace the visual display of such information or minimal audible tones (e.g., beeps) that are displayed or emitted in use of the external programmer or pacing system analyzer.

Other approaches than reliance upon RF telemetry transmissions have also been developed for providing real time warnings to the patient that the IMD is malfunctioning or is about to deliver a therapy in response to a detected need. Audible beeping alarms have been proposed to be incorporated into the IMD to warn the patient of battery depletion as disclosed for example in U.S. Pat. Nos. 4,345,603 and 4,488,555, incorporated herein by reference. Similarly, the application of low energy stimulation to electrodes on or near the IMD to "tingle" the patient upon battery depletion have been proposed in U.S. Pat. Nos. 4,140,131, and 5,076,272, incorporated herein by reference, and also in the above-incorporated '603 patent. Use of the audible beeping alarm incorporated into an implantable cardioverter/defibrillator to warn the patient of impending delivery of a cardioversion shock is disclosed for example in U.S. Pat. No. 4,210,149, incorporated herein by reference.

Moreover, it has been proposed to employ acoustic beeping warnings of implantable cardiac pacemaker battery depletion in an external monitor which apparently is directly coupled with an implanted cardiac pacemaker in U.S. Pat. No. 4,102,346. Acoustic voice recordings have been incorporated into external medical devices to provide warnings or instructions for use as disclosed in U.S. Pat. Nos. 5,285,792, 4,832,033, and 5,573,506, incorporated herein by reference.

As noted above, the historical development of IMDs has been marked by ever increasing sophistication and complexity in design and operation. However, in certain circumstances, it is desirable to provide simplified IMDs having limited features and controllable operating modes and parameters for use in developing countries or that can be controlled by the patient.

As an example of the former case, a simplified and low cost programmable, single chamber cardiac pacemaker pulse generator is disclosed in commonly assigned U.S. Pat. Nos. 5,391,188 and 5,292,342, incorporated herein by reference, specifically intended to meet demand in emerging countries. In order to avoid the need for expensive external programmers, the low cost pacemaker disclosed therein is designed to employ a simplified programming scheme and a simple EKG display coupled to skin contact electrodes for simply displaying the pacing pulse artifact and patient's ECG. In this low cost implantable cardiac pacemaker, programming is effected by repeated timed applications of the magnetic field to the IMD as described therein to incrementally increase or decrease pacing rate, pacing pulse width amplitude, etc. The magnetic field can be manually applied and removed and the field polarity can be reversed. A magnetic field sensor and associated programming circuitry within the IMD responds to the application and polarity of the magnetic field to make the incremental changes. The medical care provider must closely watch the EKG display and calculate the changes in pacing rate from the observed changes in pacing interval and scale changes in pulse amplitude. This requires good hand-eye coordination and rapid mental calculation to determine just when the desired rate or amplitude change has been accomplished.

In the latter case, neurological stimulation devices and drug delivery systems are available for implantation in a patients' body, and external programmers for providing limited adjustment of stimulation therapies and delivery of drugs are provided to the patients to allow them to adjust the delivered therapy. Such devices include the MEDTRONIC® Itrel® implantable nerve stimulator and Synchromed® drug infusion system. The patients are allowed to adjust the stimulation and drug therapies by transmitting "increase" and "decrease" commands. The implanted medical device responds to the programmed command, but the response is not communicated back to the patient who may remain concerned that the desired adjustment has not been made.

All of the above-described RF telemetry systems require complex circuitry, and bulky antennas as described above and are expensive to implement into an IMD. The RF telemetry transceiver in the IMD consumes electrical energy from the device battery while it is in use. Moreover, the telemetry systems all require use of an expensive and complex external programmer that establishes the telemetry protocol, encodes and transmits the downlink telemetry transmissions, and receives, decodes and displays and/or records the uplink telemetry transmissions. The uplink telemetered data from the IMD and device operations, e.g., delivery of pacing pulses by an implantable cardiac pacemaker, are recorded and/or displayed only visually, requiring careful visual observation by the medical care provider operating the programmer. Similarly, confirmation of acceptance of a programmed change in an operating mode or parameter value can only be observed using a recorder or visible display of a confirmation received in an uplink telemetry transmission. It is desirable to provide a simple way to confirm the acceptance of a programmed change that would not require use of RF telemetry equipment by the patient or medical care provider and RF telemetry capability in the IMD. This is especially the case in programming limited operating modes and parameter values by a patient using a limited function programmer. As will become apparent from the following, the present invention satisfies many of these needs.

SUMMARY OF THE INVENTION

The objects of the present invention are directed to improving the above-described prior art systems for confirming programming of an IMD of the above described types to increase assurance that the programmed parameter values and modes have been accepted.

It is therefore a primary object of the present invention to provide a simplified system usable in a programming sequence for audibly communicating a change in operation of an IMD implanted in a patient in an audio frequency range to the patient and/or a medical care provider to confirm the change in operation.

It is another object of the present invention to provide such a simplified system for uplink audible communication to the patient or medical care provider via voiced statements or musical tones emitted by the IMD of its current programmed operating modes, parameter values, operations, and states.

It is still another object of the present invention to provide such voiced statements or musical tones during the programming of such an IMD by a medical care provider following a simplified programming protocol employing timed, manual applications of a magnetic field to the IMD.

It is a further object of the present invention to employ an acoustic transducer and voice or musical tone recording and playback device in the IMD to accomplish the above stated objects with the minimal expenditure of device battery energy during programming thereof.

It is also an object of the present invention to provide a method and apparatus for recording and/or selecting pre-recorded voiced statements in one or more human languages in the voice recording and playback device during or following manufacture of the IMD.

It is a still further object of the present invention to employ an acoustic transducer in the IMD to accomplish the above stated objects with the additional ability to function as a patient activity sensor to provide an activity signal when it is not employed as stated above.

One preferred embodiment of the present invention that can be implemented in a variety of IMDs relates to uses of voiced statements or musical tones emitted from an IMD during programming of device operating modes or parameter values, operations and states. The voiced statements or musical tones may be listened to and understood by the medical care provider or the patient to confirm acceptance of a programming command to change an IMD operating mode or parameter value or state or to trigger an operation, e.g., a delivery of a therapy or commencement of monitoring. The present invention may be implemented in simplified, low cost programming schemes to provide the sole uplink transmission of IMD information including stored data and operating states or device operations as well as the confirmation of the programmed change thereof. The present invention may also be implemented into sophisticated RF telemetry programming and interrogation methods and protocols to selectively replace or augment uplink RF telemetry transmissions and display of IMD information and confirmation of programmed changes thereof.

Such audibly transmitted IMD information preferably includes identification of the device, its current programmed operating modes and parameter values, device or component conditions or states, e.g., its power source state, and voiced statements or musical tones accompanying real time device operations. The audibly transmitted IMD information can also include patient identification and date of implantation and date of last interrogation in IMDs capable of being programmed with such data Moreover, the audibly transmitted IMD information can also include stored physiologic data in IMDs capable of monitoring physiologic conditions and storing such data.

The preferred embodiments of the invention share the advantageous feature of providing voiced statements or musical tones conveying or signifying the programming changes simply in response to detection of a programming command applied to the IMD through the patient's skin. In one preferred embodiment, the programming command is an externally applied magnetic field or series of magnetic fields that in each case is sensed by a magnetic field sensor in the IMD and places the IMD in a programming mode to commence a programming sequence. However, the programming command can also constitute a downlink telemetry interrogation command emitted by a programmer in a conventional RF telemetry transmission session. In the programming sequence, changes in operating parameter values are made sequentially, and each change is confirmed by an audible voiced statement or musical tone. Additionally, ascending or descending scale musical tones can be emitted accompanying each incremental increase or decrease, respectively, in the programmed parameter value to signify that the parameter value is being changed. As noted below, in certain IMDs one or more ascending or descending scale musical tone can be emitted following each increase or decrease in the parameter value, and the actual value need not be voiced in an emitted voice statement.

The IMD includes an audio transducer that is driven by audio transducer drive signals retrieved from analog memory to emit the voiced statements or musical tones during the programming sequence and during interrogation sequences and the emission of a warning to the patient at other times. A plurality of audio transducer drive signals of voiced statements or musical tones conveying or signifying the above listed types of IMD information are stored in the analog memory. In a hardware embodiment, the appropriate audio transducer drive signals are accessed in both interrogation and programming sequences by logic circuitry that generates their unique memory addresses in an interrogation sequence. In a microcomputer based embodiment, a programming operating algorithm is used to sequentially generate the addresses of the appropriate audio transducer drive signals. In either case, during interrogation and programming sequences, addresses of the appropriate audio transducer drive signals are retrieved to apply the audio transducer drive signals to the audio transducer.

To conserve energy, the voiced statements or musical tones accompanying programming of the IMD are emitted by the audio transducer at a low volume that preferably cannot be heard without use of an external audio amplifier or stethoscope. However, the voiced statements or musical tones are of sufficient volume to be transmitted through the body to a location easily accessible by the medical care provider using a stethoscope or other simple audio amplifier. No RF telemetry antenna and transceiver need be employed. The medical care provider is immediately apprised of the acceptance of the programming command, the change in the programmed operating modes and parameter values, operations or states without needing to analyze visually presented data.

Optionally, a switched amplification stage is employed to advantageously amplify certain voiced statements or musical tones to a volume that can be heard by the patient and recognized as a warning to take action. Such warnings include battery energy depletion or depletion of a drug in an implantable drug delivery system, or the imminent delivery of a therapy, to alert the patient to take appropriate action.

The present invention can be very advantageously implemented into the low cost implantable pacemaker disclosed in the above-incorporated, commonly assigned '188 and '342 patents. In this low cost implantable cardiac pacemaker, programming is effected by repeated timed applications of the magnetic field of a particular polarity to the IMD as described therein to incrementally increase or decrease pacing rate, pacing pulse width, pacing pulse amplitude, etc. The present invention provides audio feedback of each changed parameter value in real time to assure the medical care provider that the change is correctly made and that no further applications of the magnet are required when the desired value has been programmed and is voiced. This implementation overcomes the difficulty in confirming the desired pacing rate and pacing pulse amplitude by calculating the escape intervals and amplitudes from the rapidly occurring pacing artifacts on the EKG display. Moreover, many other operating states, parameters and modes can be communicated by voiced statements.

The invention can be advantageously implemented into any of the IMDs listed above including those which could not employ observation of the patient's ECG or of electrical stimulation pulses. For example, in an implantable drug delivery system, the drug delivery rate and volume can be interrogated or programmed in a similar fashion. In an implantable electrical stimulator, the stimulation rate, amplitude or energy can be altered and the alteration can be confirmed by emission of voiced statements or musical tones. In these contexts, the patient can be provided with a limited function programming capability for programming changes in these parameters. The IMD can be configured using the switched amplification stage to emit the voiced statements and musical tones at a volume that the patient can hear to confirm the change.

The audio transducer drive signals are advantageously recorded in solid state, non-volatile, analog memory locations within the implantable memory device. The voiced statements are preferably recorded in the language appropriate to the patient or the country or population where the patient resides at the point of manufacture or distribution. In one embodiment where sufficient non-volatile memory is available, the voiced statements can be recorded in multiple languages, and the appropriate language can be selected for use by a programmed selection command. In the more sophisticated IMDs having RF telemetry capabilities, the specific language can be selected by a downlink RF telemetry command. In the low cost IMD, a repeated sequence of magnetic fields can be provided that, when decoded, can be used to select a language.

The capability of recording the voiced statements or selecting pre-recorded voiced statements in the locally prevailing language allows a more flexible, less error prone and safer audible feedback and control. A physician or other medical care provider can select the language of the voiced statements if a patient moves to a country or locale where the prevailing language differs from that prevailing in the country or locale departed by the patient.

The audio transducer is preferably a piezoelectric transducer that is mounted within the housing of the IMD. In the context of a programmable implantable pacemaker or monitor, the audio transducer can also be employed as a microphone or accelerometer to detect patient activity, specifically patient locomotion or vigorous limb exercises. In this context, the transducer generates activity signals in response thereto, and the pacing rate can then be adjusted to provide adequate cardiac output in a manner well known in the art.

BRIEF DESCRIPTION OF THE DRAWINGS

These and other objects, advantages and features of the present invention will be appreciated as the same becomes better understood by reference to the following detailed description of the preferred embodiment of the invention when considered in connection with the accompanying drawings, in which like numbered reference numbers designate like parts throughout the figures thereof, and wherein:

FIGS. 3a–3c are timing diagrams depicting successive applications of the magnet to the IPG of FIG. 2, and the responses of the IPG to the applied magnetic fields, including device operations and voiced statements generated in the interrogation and programming sequences;

FIG. 4 is a chart depicting the memory address locations of voiced statements emitted in the interrogation and programming sequences illustrated in FIGS. 3a–3c;

FIG. 11 is a chart depicting the memory address locations of audio transducer drive signals for emitting voiced statements or musical tones in interrogation and programming sequences of an implantable drug delivery apparatus of FIG. 10 having an operating system of FIG. 8 or 9; and FIG. 12 is a chart depicting the memory address locations of audio transducer drive signals for emitting voiced statements or musical tones in interrogation and programming sequences of an implantable electrical stimulation apparatus of FIG. 10 having an operating system of FIG. 8 or 9.

DETAILED DESCRIPTION OF THE PREFERRED EMBODIMENTS OF THE INVENTION

Figure 1:
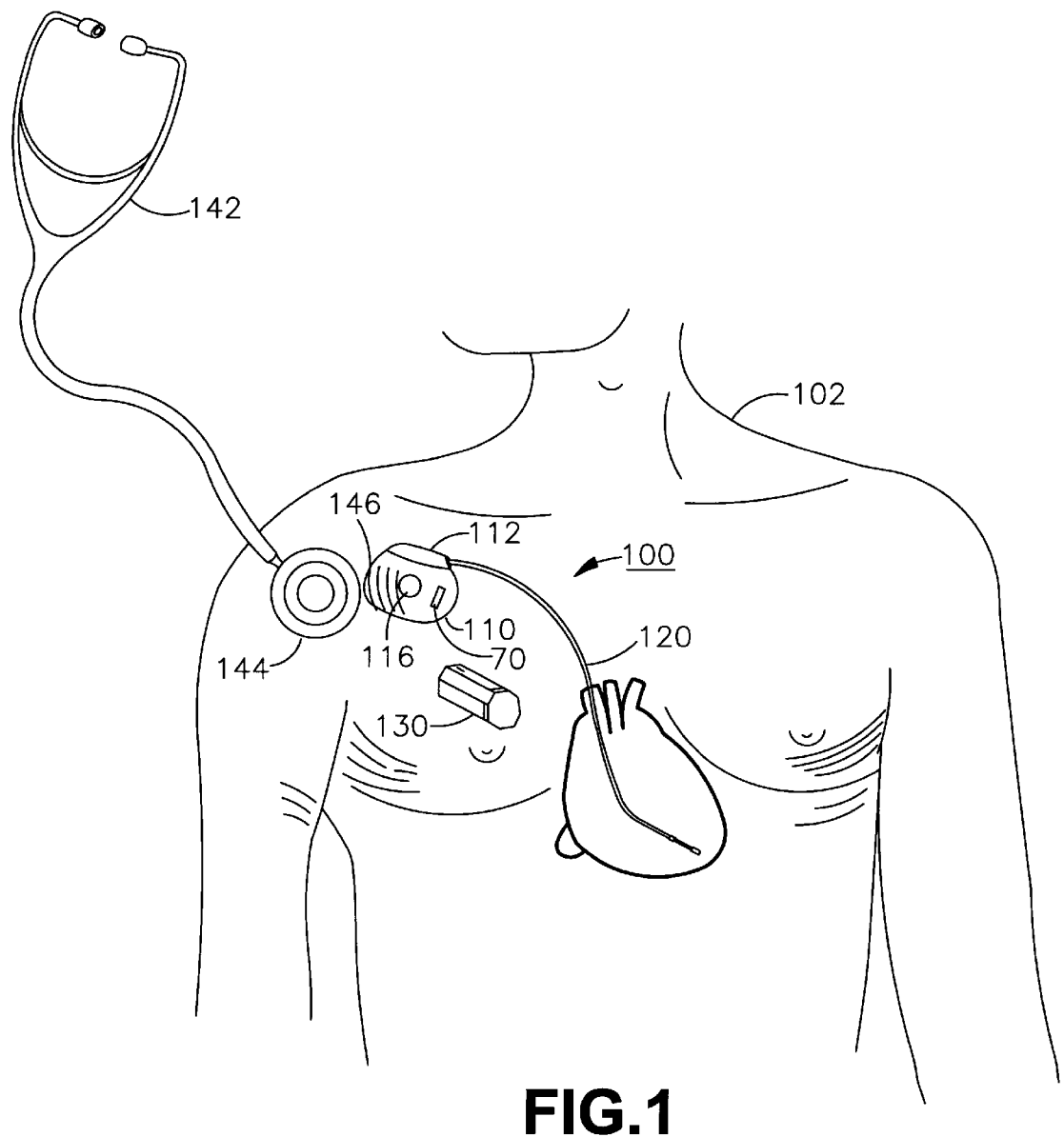
FIG. 1 is a simplified schematic view of communication between a programmable IMD in a patient and a medical care provider effecting interrogation and programming thereof using audible voiced statement or musical tone feedback from the IMD.

The preferred embodiments of the present invention disclose uses of audio voiced statements or musical tones emitted from an IMD in the course of a communication session involving interrogation or programming of device operating modes or parameters or to provide a patient warning. The musical tones or voiced statements can may be listened to by the physician or other medical care provider to augment or substitute for visual displays or to otherwise confirm programming changes or listened to by the patient to confirm patient initiated programming. The present invention may be implemented in all of the above referenced IMDs that provide monitoring and/or delivery of a therapy to a patient. The present invention may be implemented in simplified, low cost programming schemes to provide the sole uplink transmission of IMD information. The audible voiced statements preferably also assist the medical care provider in following a programming or interrogation protocol during an initial implantation or follow-up session. The present invention may also be implemented into sophisticated RF telemetry programming and interrogation methods and protocols to selectively replace or augment uplink RF telemetry transmissions of device operating modes, states, operations and parameter values.

The IMD includes an audio transducer that emits musical tones or voiced statements decoded from code stored in device memory correlated to a device operating mode, state, operation, or parameter value following an interrogation and programming protocol. To conserve energy, the musical tones are short in duration, and the voiced statements are at a low volume that preferably cannot be heard without use of an external audio amplifier or stethoscope. The use of the audio transducer with a switched amplification stage advantageously also allows the emission of voiced warnings of battery energy depletion, device malfunction, or imminent delivery of a therapy at an amplitude that is sufficient to be heard by the patient, so that the patient can take appropriate action. Moreover, in the context of a low cost, programmable implantable pacemaker, the audio transducer can also be employed as a microphone or accelerometer to detect patient activity, specifically patient locomotion or vigorous limb exercises. The transducer generates activity signals in response thereto, and the pacing rate can then be adjusted to provide adequate cardiac output in a manner well known in the art.

The following description in reference to FIGS. 1–7 is directed to various preferred embodiments of the invention implemented in the housing of a low cost, single chamber, implantable cardiac pacemaker IPG that is programmed using a permanent magnet. This implementation can be incorporated into a more complex, dual chamber, programmable pacemaker or pacemaker/cardioverter/defibrillator IPG as described in reference to FIGS. 8–10. Other uses of audible communications attendant to programming or interrogation of the IMDs identified in FIG. 10 are then described. Particular uses with implantable drug delivery systems and implantable electrical stimulators are illustrated in FIGS. 11 and 12, respectively. Those of skill in the art will be readily able to adapt the teachings found herein to the IMDs listed herein and others to be devised in the future.

FIG. 1 is a simplified schematic illustration of the audio feedback of data from an IMD 100 implanted in a patient 102 that occurs during interrogation or during programming to confirm changes in device operating mode or parameter values. For convenience of illustration, the IMD 100 is preferably a cardiac pacemaker comprising a pacemaker IPG 110 and a pacing lead 120 which extends from the IPG connector 112 to one or more pace/sense electrodes located in or on the patient's atrium or ventricle in the conventional manner. The pacemaker IPG 110 is therefore illustrated as either a programmable, single chamber atrial or ventricular IPG operating in an atrial demand or ventricular demand pacing mode. Moreover, in the preferred embodiments described below, the pacemaker IPG 110 has the operating architecture of the low cost, single chamber pacemaker IPG disclosed in the above-incorporated, commonly assigned '188 and '342 patents incorporating the audio feedback features of the present invention as described below.

In the embodiment of FIGS. 2–7, a communication session is established with the IMD by application and removal of the permanent magnet 130 by the physician or other medical care provider to the patient's skin over the IPG 110 according to protocols described below. The magnetic field constitutes a communication link signal that is detected by the IPG 110 to establish the communication session. The interrogation of IMD information and programming of the pacemaker IPG 110 operating modes and parameter values is effected during the communication session.

The magnetic field polarity is sensed by a magnetic field sensor 70 within the housing of the pacemaker IPG 110. The interrogation and programming protocol is recognized by decoding and logic circuitry coupled to the magnetic field sensor in a manner described below. In accordance with the low cost pacemaker preferred embodiments of the invention, each protocol causes stored voiced statements to be emitted by an audio transducer 116 disposed on or within the IPG housing as acoustic waves 146 audible to a physician, the acoustic waves being conducted through the body of the patient 102. The physician or other medical care provider employs a stethoscope 142 by applying the horn 144 to the patient's skin and listening for the voiced statements a acoustic waves 146 while applying and removing the magnet 130 to the patient's skin in the sequence established by the protocol. While not specifically illustrated, it will be understood that the medical care provider can also use an EKG display or recorder to observe pacing pulse artifacts in the manner described in the above-incorporated, commonly assigned '188 and '342 patents. To conserve energy, the voiced statements accompanying interrogation and programming of the IMD are at a low volume that preferably cannot be heard without use of an external audio amplifier or the stethoscope 142.

In the context of a low cost, programmable implantable pacemaker, the audio transducer 116 can also be employed as a microphone or accelerometer to detect patient activity, specifically patient locomotion or vigorous limb exercises. The transducer 116 generates activity signals in response thereto, and the pacing rate can then be adjusted to provide adequate cardiac output in a manner well known in the art and described, for example, in commonly assigned U.S. Pat. No. 5,080,096, incorporated herein by reference.

Figure 2:
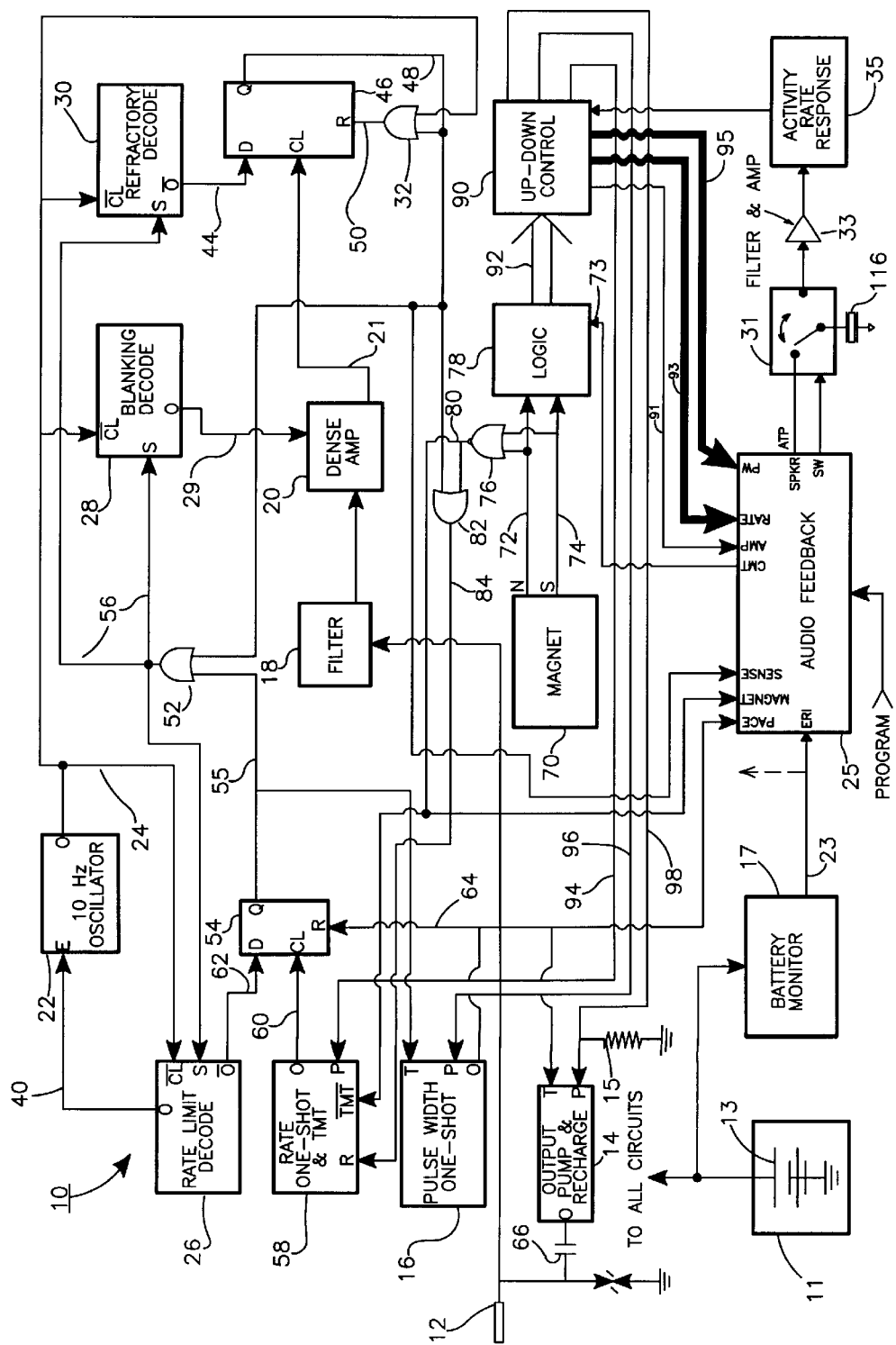
FIG. 2 is a block diagram of an exemplary pacemaker implantable pulse generator (IPG) circuit employed in the system of FIG. 1 and operated in accordance with FIGS. 3a–3c and 4 when a magnet is applied to the patient's skin over the IPG.

FIG. 2 is a block diagram depicting the major components of a small, lightweight, limited function, implantable pacemaker IPG circuit 10 in accordance with one embodiment of the present invention and is a modification of FIG. 1 of the above-incorporated, commonly assigned '188 and '342 patents. The modification involves the incorporation of battery monitor circuit 17, the audio feedback circuit 25, the acoustic transducer 116, electronic switch 31, filter and amplifier circuit 33, and optional activity rate response circuit 35, and connection lines with certain of the other circuit blocks. It should be understood that the even numbered circuit blocks in FIG. 2 may take the form of those circuits disclosed in detail in the above-incorporated, commonly assigned '188 and '342 patents and equivalents thereto. Specific embodiments of those circuits have also been identified in the above-incorporated, commonly assigned '188 and '342 patents with reference to prior patents for the purposes of illustration only. References to such circuits is not intended to limit the scope of the present invention to particular implementations of these circuits. It is believed by the inventors that the selection of particular circuits is not critical to the present invention so long as they function as a whole to perform the operations of the present invention.

Pacemaker IPG circuit 10 is encased within a hermetically sealed housing of IPG 110 implanted within the patient 102 and is coupled at IPG connector 112 to an atrial or ventricular cardiac pacing lead 120 as shown in FIG. 1. Pacemaker IPG circuit 10 provides single chamber pacing and may be used in conjunction with a ventricular pacing lead or an atrial pacing lead to provide ventricular or atrial demand pacing in the conventional VVI or AAI and related programmable pacing modes.

It is to be understood throughout the present disclosure that various internal electronic components comprising pacemaker IPG circuit 10 are coupled to a power source 11, including a battery 13, e.g., a commercially available magnesium oxide ($MnO_2$) camera battery or the like. For the sake of clarity, the connection of all of the circuit blocks with power source 11 is not shown in FIG. 2. However, the power source 11 is shown coupled with a battery monitor 17 for providing a warning trigger signal representative (in this case) of battery voltage to the Elective Replacement Indicator (ERI) input of audio feedback circuit 25 to trigger a voiced battery status during device interrogation as described below in reference to FIGS. 3a–3c. In accordance with another aspect of the present invention, the warning trigger signal also can be used to periodically trigger the generation of an audible sound that can be heard by the patient to alert the patient that the battery voltage is depleted and to take appropriate action, The battery monitor 17 periodically compares the output voltage of the battery 13 against a reference voltage therein selected to provide the ERI warning trigger signal to the ERI input when battery voltage falls below the reference voltage. Such a battery monitor 17 follows the teachings of commonly assigned U.S. Pat. No. 4,313,079, incorporated by reference herein. Although it is not depicted in this embodiment, it will be understood that the ERI signal can also be applied to the up-down control circuit 90 to adjust the pacing rate to a percentage of the programmed pacing rate and applied to the activity rate response circuit 35 (if present) to disable it's operation. For example, the up/down circuit 90 is responsive to the ERI signal to adjust a programmed pacing rate of 70 ppm downward to an ERI rate of 58 ppm, for example, during normal VVI or AAI pacing.

Pacemaker IPG circuit 10 includes an output and pump circuit 14 which responds to a pacing trigger signal generated by pulse width one-shot 16 by delivering pacing (PACE) pulses to terminal 12 and the atrial pacing lead or ventricular pacing lead attached to it. Output and pump circuit 14 may correspond generally to the pacing pulse output circuit disclosed in commonly assigned U.S. Pat. No. 4,476,868 incorporated by reference herein or other conventional pacing pulse output circuits. Output and pump circuit 14 further includes a programmable amplitude control circuit disclosed in detail in the above-incorporated '342 patent which allows for programming the pacing pulse amplitude by way of an amplitude programming signal applied to the pump (P) input. In the preferred embodiment, the pacing pulse amplitude is programmable between a high, medium and low amplitude.

The patient's intrinsic electrical cardiac activity is monitored by means of a conventional filter circuit 18 and sense amplifier 20 coupled to terminal 12 for filtering and amplifying intrinsic electrical cardiac signals from the patients heart. Filter circuit 18 performs basic band-pass filtering operations on the raw atrial or ventricular electrical cardiac signal, and provides the conditioned signal to the input of a conventional sense amplifier 20. The sense amplifier 20 is configured to detect a P-wave or R-wave and provide a SENSE output signal on line 21. The SENSE output of sense amplifier 20 is conducted on line 21 to the clock (CL) input of D flip-flop 46.

In accordance with this embodiment of the present invention, timing operations of pacemaker IPG circuit 10 is controlled by a slow, e.g., 10 Hz, master timing clock signal generated by 10 Hz oscillator circuit 22 which is enabled via line 40 from one output of rate limit decode circuit 26. The 10 Hz oscillator circuit 22 is shown and described in detail in reference to FIG. 10 of the above-incorporated, commonly assigned '188 and '342 patents. Each time that the 10 Hz oscillator circuit 22 is enabled, it emits four 10 Hz pulses over a 400 mSec time period; then it remains dormant until it is enabled again. The 10 Hz timing clock signal generated by oscillator circuit 22 is applied via line 24 to the negative CL inputs of a rate limit decode circuit 26, a blanking decode circuit 28 and a refractory decode circuit 30, and to one input of an AND gate 32. Rate limit decode circuit 26, blanking decode circuit 28, and refractory decode circuit 30 define an upper rate limit period, a blanking period, and a refractory period, respectively, by counting 10 Hz clock cycles provided on line 24 to their negative CL inputs.

The conventional blanking circuit 28 provides a blanking signal to sense amplifier 20 when a Pacing pulse is delivered or a SENSE signal is generated that extends therefrom for a blanking interval, e.g., 100 mSec corresponding to one 10 Hz clock cycle. It is to be understood that a blanking period comprising a greater number of clock cycle counts may be defined, depending upon the desired length of the blanking interval and the actual oscillation rate of oscillator circuit 22. The blanking signal effectively disconnects the input of the sense amplifier from the terminal 12 for the blanking time period to allow pacing pulse induced artifacts that would otherwise saturate sense amplifier 20 to dissipate and to avoid double sensing of an intrinsic P-wave or R-wave.

Refractory decode circuit 30 defines a refractory period which follows every SENSE or PACE cardiac event. Refractory decode circuit 30 measures the refractory period by counting 10 Hz clock cycles from line 24, just as blanking decode circuit measures the blanking interval. In the presently preferred embodiment of the invention, it is believed that a refractory period on the order of 300 mSec or so is appropriate. In that instance, refractory decode circuit 30 can define the refractory period as lasting for three 10 Hz clock cycles.

A logic low level refractory output signal is provided by refractory decode circuit 30 during the refractory period on line 44 and is applied to the D input of a D flip-flop 46. The output on line 21 from sense amplifier 20 is applied to the CL input of flip-flop 46. The Q output of D flip-flop 46 is maintained at a logic low level and cannot be switched to a logic high level as long as the logic low level refractory output signal is provided by refractory decode circuit 30 to the D input. But, after the refractory period has expired, the refractory signal on line 44 applied to the D input returns to a logic high level. At this point, the assertion of a SENSE signal on line 21, caused by a sensed event as described below, clocks the Q output of D flip-flop 46 on line 48 to a logic high level, non-refractory sense signal.

The logic high or low level on line 48 is applied to one input of AND gate 32; and the 10 Hz clock signal is applied to the other input of AND gate 32, as previously noted. If the refractory period has not expired, the output of AND gate 32 and the signal level on line 50 remains at a logic low level. If the refractory period has expired, line 48 will go to a logic high level upon detection of a SENSE event. A SENSE signal on line 21 occurring after expiration of the 300 mSec refractory period switches the Q output of D flip-flop 46 to a logic high level. Then, the next positive excursion of the 10 Hz clock signal will switch the output of AND gate 32 to a logic high level. The output of AND gate 32 is conducted on line 50 to the reset (R) input of flip-flop 46. In this way, the Q output of D flip-flop 46 is switched to a logic low level when the signal on line 50 goes to a logic high level at the next clock signal following a sense signal that occurs after expiration of the refractory period.

The non-refractory sense signal on line 48 is also applied to one input of an OR gate 52, and the pulse width trigger signal on line 55 is applied to the other input of OR gate 52. The output of OR gate 52 is conducted on line 56 to the set (S) inputs of rate limit, blanking and refractory decode circuits 26, 28, and 30. A logic high level pulse on line 56 corresponding to either a non-refractory sense signal or a pulse width trigger signal sets and restarts the upper rate limit interval, blanking interval, and refractory interval. In addition, when the rate limit decode circuit is set, it applies the logic high level enabling signal on line 40 to enable the 10 Hz oscillator circuit 22 which again emits the four, 10 Hz clock pulses.

Rate limit decode circuit 26 defines an upper rate limit for delivery of stimulating pulses by pacemaker IPG circuit 10. In the presently disclosed embodiment of the invention, it is believed that an upper rate limit of one pacing pulse every 400 mSec, or a maximum pacing rate of 150 PPM, is appropriate. In this case, rate limit decode circuit 26 defines an upper rate limit interval which lasts for the four successive 10 Hz clock cycles applied to its CL input. The output O from rate limit decode circuit 26 goes to a logic low level for the 400 mSec period when the logic high level signal on line 56 is applied to the S input of rate limit decode logic 26 following each SENSE and PACE event as described above. This logic low level signal is applied on line 62 to the D input of D flip-flop 54, and it prevents the D flip-flop output Q from being switched from a logic low level to a logic high level in response to a logic high level or transition at the CL input of D flip-flop 54. After the 400 mSec upper rate limit interval has elapsed, the O output signal on line 62 from rate limit circuit 26 returns to a logic high level.

A rate one-shot and TMT circuit 58 (hereinafter referred to simply as rate/TMT circuit 58) determines the base pacing rate, which is the rate at which pacing pulses are delivered to terminal 12 in the absence of a SENSE output on line 21 during the pacing escape interval. The pacing escape interval between output pulses produced by rate/TMT circuit 58 at its output O is programmable, within a range from 460 to 1200 mSec to establish programmable pacing rates in 10 PPM increments between 130 PPM and 50 PPM, respectively, for example. Rate/TMT circuit 58 includes a re-triggerable monostable multivibrator which produces an output signal at its output (O) that is applied to the CL input of D flip-flop 54 via line 60 when the programmed escape interval times out. If the 400 mSec upper rate period has timed out, the Q output of D flip-flop 54 is switched to a logic high level in response to the output signal on line 60, providing a pulse width trigger signal to the trigger (T) input of the pacing pulse one-shot 16 via line 55. During the 400 mSec upper rate interval, an output signal on line 60 from rate/TMT circuit 58 cannot switch the Q output of the D flip-flop 54 to a logic high level and generate the pulse width trigger signal.

At this point, it should be noted that a logic high level pulse width trigger signal on line 55 is also directed through the OR gate 52 and line 56 to the S inputs of rate limit, blanking and refractory decode circuits 26, 28, and 30. The logic high level pulse width trigger signal on line 56 restarts the upper rate limit interval, blanking interval, and refractory interval on expiration of the pacing escape interval following expiration of the 400 mSec rate limit interval.

The programmed pacing escape interval is automatically restarted within the rate/TMT circuit 58 when the output pulse is generated on line 60. The programmed pacing escape interval is also restarted in the rate/TMT circuit 58 in response to a SENSE event. A rising edge transition of a reset signal occurring on line 84 from the output of AND gate 82 that is applied to the R input of rate/TMT circuit 58 restarts the pacing escape interval. The non-refractory sense signal on line 48 from the Q output of D flip-flop 46 is coupled to one input of AND gate 82, and the normally logic high level output of NOR gate 76 is coupled to the other input of AND gate 82. The Q output of the D flip-flop 46 goes to a logic high level in response to a SENSE event on line 21 after expiration of the refractory interval indicating a non-refractory sense event. The rising edge transition is conveyed via line 48, AND gate 82 and line 84 to the R input of rate/TMT circuit 58 and restarts the pacing escape interval. As long as a rising edge transition appears at the R input of rate/TMT circuit 58 more frequently than the programmed pacing escape interval, the output signal on line 60 will stay at a logic low level, and generation of pulse width trigger signals at the Q output of D flip-flop 54 will be inhibited.

The pulse width trigger signal output by flip-flop 54 is conducted on line 55 to the T input of pulse width one-shot 16 which responds by producing a pace trigger pulse on line 64 having a duration that defines the pulse width of the pacing pulse produced by output and pump circuit 14. The pacing pulse width is programmable within a range from 0.1 to 1.0 mSec, for example, in a manner described in greater detail in the above-incorporated, commonly assigned '188 and '342 patents. Pace trigger pulses output from pulse width one-shot 16 are applied via line 64 to the T input of output and pump circuit 14 which responds by applying the programmed amplitude pacing pulse to terminal 12 and the pacing lead attached to it via coupling capacitor 66. Pace trigger pulses from pulse width one-shot 16 are also applied on line 64 to the R input of D flip-flop 54 to terminate the pulse width trigger signal by terminating the logic high level latched or stored at the Q output of D flip-flop 54.

In this manner, pacing pulses are generated on demand and applied to the pacing lead depicted in FIG. 1 The programming of the pacing rate and pacing pulse amplitude and width is accomplished in this embodiment in the manner described and illustrated in detail in the above-incorporated, commonly assigned '188 and '342 patents. The programming circuitry and protocol disclosed therein utilizes a solid state semiconductor device which is sensitive to application of an external magnetic field in order to eliminate the conventionally used, costly, bulky, and energy consuming RF telemetry circuitry and components. A solid-state magnetic field sensor (MAGFET) 70 suitable for use in an IMD telemetry system is disclosed in commonly assigned U.S. Pat. No. 5,438,990 to Wahlstrand et al., incorporated herein by reference in its entirety. In the absence of an applied magnetic field, both the N and S output signals on lines 72 and 74 are at a logic zero or low level. As noted in the '990 patent, MAGFET circuit 70 is capable of discerning between external magnetic fields of two different polarity orientations (e.g., between a field oriented north-south and a field oriented south-north). Accordingly, MAGFET circuit 70 produces two logic high output signals, N (north) on line 72, and S (south) on line 74. The N signal is asserted, for example, upon detection by MAGFET circuit 70 of an applied magnetic field of N-S orientation. Similarly, the S signal is asserted upon detection of an applied magnetic field of S-N orientation.

Logic circuit 78 receives the logic high level N or S signal on line 72 or 74 from MAGFET circuit 70. Logic circuit 78 detects applications of the magnetic field in the N-S or S-N field orientation, respectively, and removals of the magnetic fields. As illustrated below in reference to FIG. 3b, logic circuit 78 issues control signals to an up/down control circuit 90 via a plurality of control lines designated collectively as 92 in FIG. 2. Logic circuit 78 includes digital logic circuitry for detecting and counting magnet removal and replacement cycles as described in the above-incorporated, commonly assigned '188 and '342 patents and asserts various control signals in response thereto for effecting programming of pacing rate, pacing pulse width and pacing pulse amplitude.

For example, in response to detection of one magnet removal/replacement cycle, logic circuit 78 asserts a control signal to up/down control circuit 90 causing it to enter a pacing rate programming mode. In the rate programming mode, another control signal is derived from the N or S magnet polarity signal on line 72 or 74 that orders that the pacing rate is to be incrementally increased or decreased, respectively.

Up/down control circuit 90 produces a plurality of output signals which are conducted on lines 94, 96, and 98 to the program (P) inputs of rate/TMT circuit 58, pulse width one-shot 16, and output/pump circuit 14, respectively. The signals on lines 94, 96, and 98 are analog reference currents which are described in detail in the above-incorporated, commonly assigned '188 and '342 patents. The reference currents on lines 94 and 96 determine the duration of output pulses from the rate/TMT circuit 58 and the pulse width one-shot 16, respectively, and hence determine the programmed pacing rate and pulse width. The reference current on line 98 determines the output pulse amplitude from the output/pump circuit 14 by generating a reference voltage on resistor 15. This reference voltage is used in conjunction with a comparator and a charging circuit in output/pump circuit 14 to charge an output capacitor to a programmed voltage amplitude as is well known in the art.

For example, in the case of the pacing rate parameter, up/down control circuit 90 provides a reference current on line 94 to the P input of rate/TMT circuit 58. An incremental decrease in the reference current level on line 94 results in an increase in the pacing escape interval established by rate/TMT circuit 58. Similarly, an incremental increase in the reference current level on line 94 results in an incremental decrease in pacing interval established by rate one-shot 58. Pulse width one-shot 16 is controlled in a similar fashion by the reference current on line 96. The pacing pulse amplitude of the pacing pulse generated by output/pump circuit 14 is directly controlled by the voltage developed on resistor 15 which is in turn controlled by the voltage on line 98 developed by up-down control circuit 90.

The interrogation and programming protocol of this embodiment of the invention is based upon initially detecting the application of the external magnetic field as illustrated in FIG. 1 and initially entering the TMT mode. Following completion of the TMT and interrogation mode, the external magnet 130 is removed and applied again successively in accordance with the protocol disclosed in the above-incorporated, commonly assigned '188 and '342 patents for programming operating modes and parameter values and the like. The number of programmable modes and parameter values of pacemaker IPG circuit 10 is relatively more limited than is typically the case with more sophisticated programmable cardiac pacemakers. For example, in this embodiment, the base pacing rate, pacing pulse width, and pacing pulse amplitude parameters are programmable within selected ranges. A single chamber asynchronous and triggered pacing mode and other parameters, e.g., sense amplifier sensitivity, refractory period, and activity thresholds and gain factors described in the above-incorporated, commonly assigned '096 patent, could be made programmable. The pacing upper rate limit and A-V delay interval could also be made programmable in a programmable dual chamber pacemaker context. There must be some arrangement for selecting which parameter or mode is to be programmed in order to separately program the different parameter values and operating modes. The identification of the parameter or mode to be programmed has been accomplished in some prior pacemakers by downlink RF telemetry transmitting a code identifying it together with the new value or mode to the receiver of the implanted pacemaker.

In the TMT mode, the rate/TMT circuit 58 provides a preset number, e.g., three, output pulses on line 60 at a TMT pacing rate to the D flip-flop 54 to provide three corresponding pulse width trigger pulses at its Q output. The non-refractory sense event signals that might be generated by D flip-flop 46 in response to SENSE signals are blocked from resetting the rate/TMT circuit 58. The AND gate 82 is blocked by the logic low level signal output on line 80 from NOR gate 76 caused by a logic high (N or S) level on one of its inputs. In this manner, the amplifier circuit 20 continues to operate but its output signals are effectively disabled as long as a magnetic field is sensed by the MAGFET 70.

The asynchronous TMT sequence assists the medical care provider in determining whether the currently programmed, pacing pulse width and pulse amplitude settings are sufficient to achieve "capture" of the patient's heart, that is sufficient to cause it to contract. The TMT sequence in the presently disclosed embodiment of the invention may be one such as is disclosed in commonly assigned U.S. Pat. No. 4,273,132 to Hartlaub, incorporated herein by reference in its entirety. The pacing pulses generated during the TMT sequence can have a higher than normal pacing rate to distinguish the TMT sequence from the asynchronous pacing pulses that precede and follow it. At least one of the TMT pacing pulses is reduced either in amplitude or pulse width to a percentage of the programmed amplitude or pulse width. In the conventional programming system described in the above-incorporated '132 patent, the medical care provider observes the patients cardiac activity on an EKG monitor during this time and observes whether or not the three pacing pulses all result in a cardiac contraction. If one (or more) TMT pacing pulse does not capture the heart, the medical care provider can increase either the programmed pulse width or pulse amplitude and conduct the TMT sequence again to verify that the pacing pulse energy is sufficient to capture the heart with an adequate safety margin.

After rate/TMT circuit 58 performs the TMT, the IPG circuit 10 commences asynchronous pacing at a nominal rate, e.g., 70 PPM, or at the programmed rate or at the ERI rate, if that function is employed, for as long as either the N or S magnetic field continues to be detected by MAGFET 70. According to the operating modes described in the above-incorporated, commonly assigned '188 and '342 patents, a protocol of manual removals and re-applications of the N or S magnetic field by appropriate movements of the poles of magnet 130 in FIG. 1 is followed to program pacing rate, pulse width and/or amplitude.

Referring to FIG. 2, the following operations are accomplished within the audio feedback circuit 25 in a manner to be described in greater detail below. Briefly, when the N or S signal is generated on lines 72 or 74, the output signal of the NOR gate 76 is applied on line 80 to the audio feedback circuit 25 as a MAGNET signal. The audio feedback circuit 25 responds to the MAGNET signal by applying the switch (SW) signal to the electronic switch 31 which responds by connecting the audio transducer 116 to the speaker (SPKR) output until the interrogation and programming protocol is completed. The MAGNET signal also causes power to be applied from power supply 11 to components of the audio feedback circuit 25 described below which are normally not powered in order to conserve energy of battery 13. The audio feedback circuit 25 includes logic circuitry for designating memory addresses for the analog voiced statements which are retrieved from analog memory and applied as audio transducer drive (ATD) signals to the audio transducer 116 to be voiced as described below.

The pace trigger signals on line 64 and the non-refractory SENSE output signals of the flip-flop 46 on line 48 are conducted to the respective PACE and SENSE inputs of the audio feedback circuit 25. Signals representative of the pacing pulse amplitude, pacing rate and pacing pulse width established in up/down control circuit 90 are conducted on lines 91, 93 and 95 to the AMP, RATE and PW inputs, respectively, of the audio feedback circuit 25. The ERI signal on line 23 is applied to the ERI input of audio feedback circuit 25 when battery voltage falls below the reference voltage in battery monitor 17 as described above.

The audio feedback circuit 25 also includes a PACE/SENSE event counter that is activated to count PACE trigger pulses and SENSE event signals occurring after the MAGNET signal is received. The event counter initially counts the PACE trigger pulses of the TMT sequence and then counts the asynchronous PACE trigger pulses during the asynchronous interrogation mode for as long as the MAGNET signal is present. In the illustrated embodiment, upon termination of the MAGNET signal, the PACE/SENSE counter counts a fixed number of PACE trigger signals and SENSE signals. That count (CNT) is applied on line 73 to the logic circuit 78 for timing re-applications of the magnetic field. The count of the PACE/SENSE event counter is used to address voiced statements to be emitted in time synchronization with each PACE and SENSE event.

In accordance with this embodiment of the present invention, audio feedback circuit 25 and audio transducer 116 are energized during the TMT to emit the voiced statement "PACE" at each pacing pulse of the TMT and "TMT PACE" at the delivery of the final reduced energy pacing pulse of the sequence. The PACE/SENSE event counter count is used to append the correct voiced statement to the pacing pulses delivered in the TMT sequence. Then, a series of voiced statements are emitted in an interrogation sequence commencing after the TMT and continuing until they are completed, whether or not the magnetic field continues to be applied. In the embodiment of FIGS. 24, the voiced statements include, manufacturer, device model and serial number identification, battery status, and parameter values including pacing rate, pacing pulse width, and pacing pulse amplitude. However, if the pacing mode and other operating parameters, e.g. sense amplifier sensitivity, refractory period, activity threshold, etc., are made programmable, then the voiced statements could include other statements of such programmed modes and parameter values.

Fixed rate pacing pulses are delivered following completion of this TMT sequence as long as the magnetic field is not disturbed. In accordance with this embodiment, the delivery of each pacing pulse is accompanied by a voiced "PACE" statement until the magnetic field is removed. In an alternative variation, only a fixed number of the "PACE" statements may be voiced, and the magnetic field may be left in place to maintain fixed rate pacing for prolonged diagnostic or treatment purposes. The emission of the "PACE" statements ceases when a fixed count, e.g., ten, of the PACE/SENSE event counter is reached. The PACE/SENSE event counter can be turned off at that point or can continue to count PACE trigger signals. Moreover, when the magnetic field is thereafter removed, a fixed number of asynchronous pacing pulses can be delivered accompanied by the voiced "PACE" statement to assist timing of re-application of the magnetic field to enter the programming mode.

The pacing mode returns to the programmed mode, which is typically the AAI or VVI mode, but could be a triggered mode (AAT or VVT), if no magnetic field is re-applied and sensed during the delivery of the fixed number of asynchronous mode pacing pulses. It would be possible to temporarily place the IPG in an inhibited mode to determine for certain whether intrinsic cardiac events are being sensed, but such a test may not be safe for the patient. Preferably, the voiced "PACE" or "SENSE" statements are emitted for a further fixed number, e.g., ten, of PACE trigger or SENSE event signals counted by the PACE/SENSE event counter following removal of the magnetic field and termination of the asynchronous mode. The PACE trigger pulse at the end of the pacing escape interval in the absence of a non-refractory SENSE event continues to be accompanied by a voiced "PACE" statement until the count is reached. As shown in FIG. 2, non-refractory SENSE events are counted and trigger emission of the "SENSE" statement, but it is possible to alternatively count and emit the "SENSE" statement on both refractory and non-refractory SENSE events.

Figure 3A:
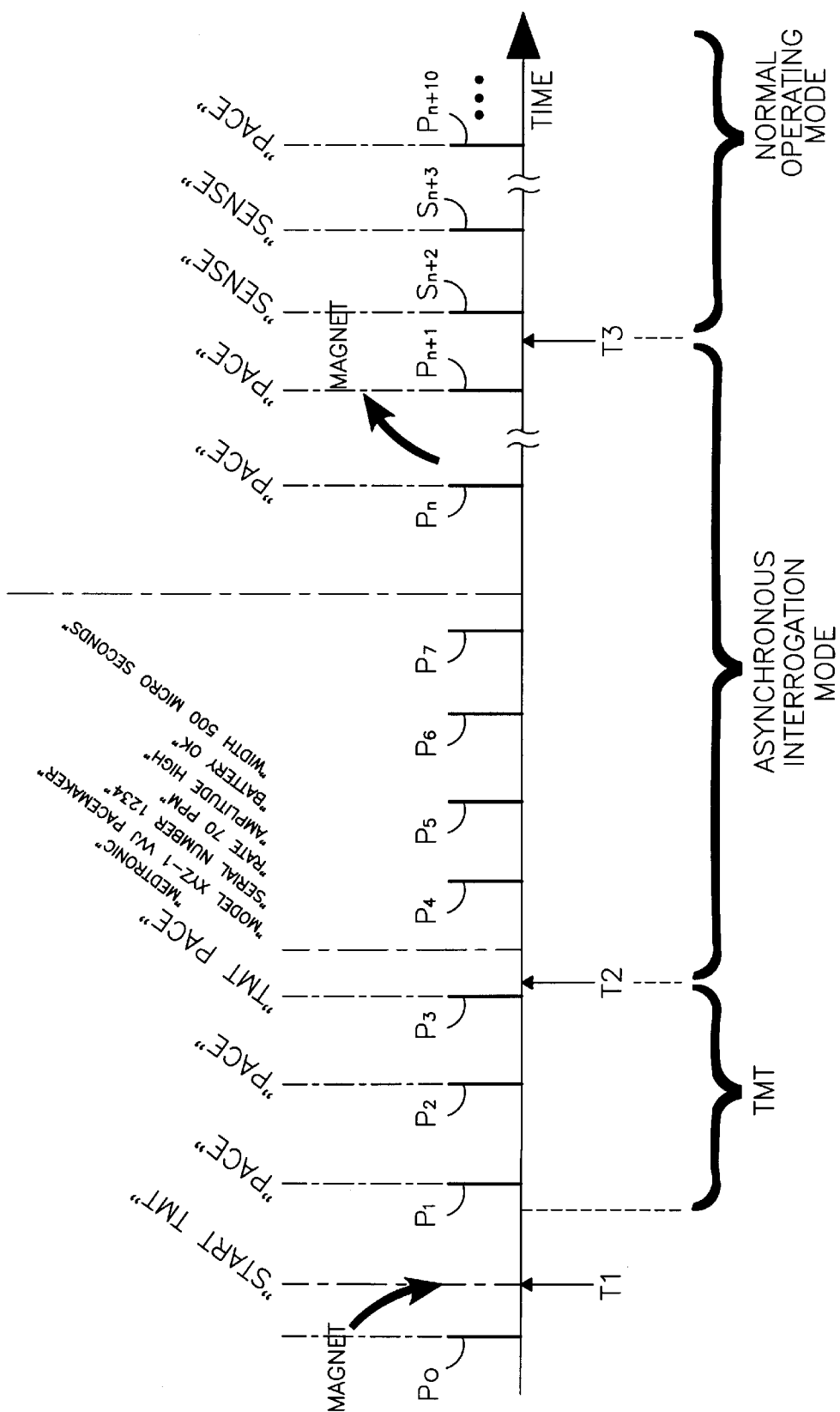

One preferred embodiment in the sequence of events involved in interrogating and/or programming pacemaker IPG 10 may be better understood with reference to the time lines of FIGS. 3a, 3b and 3c. In FIGS. 3a, 3b, and 3c, pacing pulses are represented by solid vertical lines designated $P_0$, $P_1$, etc. and sense events are represented by broken vertical lines designated $S_1$, $S_2$, etc. FIG. 3a depicts the interrogation of the pacemaker IPG identification, the programmed pacing rate and pulse amplitude, the battery condition and the voiced pace and sense events. In FIG. 3a, it is assumed that pacemaker IPG 10 is operating normally up to time T1, at which time the magnet 130 is applied as shown in FIG. 1. In response to detection of the programming magnet at T1, pacemaker IPG circuit 10 commences the TMT delivery of three pacing pulses $P_1$, $P_2$, and $P_3$ at the asynchronous rate of 100 PPM, for example. Pacing pulses $P_1$ and $P_2$ are at the programmed pulse amplitude, but pacing pulse $P_3$ is at a reduced pulse amplitude to determine if the patient's heart can be captured by the reduced energy pacing pulse. Artifacts of these three pacing pulses may be observed by a medical care provider on an EKG monitor, which also shows the PQRST complex evoked by the pacing pulse if the pacing pulse energy exceeds the patient's pacing threshold. The voiced "START TMT" statement is emitted by audio transducer 116 shortly after the MAGNET signal is generated, and the "PACE", "PACE" and "TMT PACE" statements are emitted synchronously with the next three PACE trigger signals of the TMT sequence.

Pacemaker IPG circuit 10 remains in the asynchronous (AOO) or VOO) mode in which pacing pulses $P_4$ through $P_n$ are delivered at the programmed or nominal asynchronous rate, e.g., 70 PPM, after the TMT sequence is completed at time T2 in FIG. 3a. Alternatively, the asynchronous rate may be the decreased rate of 58 ppm if the ERI signal is present and applied to the up/down control circuit 90 as described immediately above. It is to be understood that the interval of asynchronous pacing between time T2 and time T3 in FIG. 3a may last an indefinite period of time, so long as the programming magnet 130 remains in place. However, the voiced "PACE" statements may continue only until a predetermined number "n" are voiced and then stop to save battery energy. At time T3, the magnet is removed, and the pacemaker IPG returns to the programmed pacing mode, e.g., the AAI or VVI mode, at the programmed pacing rate and pacing pulse amplitude and width. Alternatively, a further number, e.g., ten, asynchronous pacing pulses can be delivered after T3 and prior to the reversion to the programmed pacing mode. This feature allows the removal of the magnet at any time after T1 and allows the TMT, uplink telemetry, and asynchronous pacing to continue to completion after such removal as just described above.

Returning to time T2, the audio feedback circuit 25 commences to retrieve and apply ATD signals to the audio transducer 116 in the depicted interrogation sequence to cause the audio transducer 116 to emit the analog voice statements. In this example, the voiced statements include a number of phrases selected from those depicted in the memory address list of FIG. 4. The pacemaker manufacturer, model and unique serial number are spoken, followed by the voiced phrases stating the programmed pacing rate, the programmed pulse width, the programmed high, medium or low pacing pulse amplitude, and the battery status. The battery status is voiced "BATTERY OK" if the logic level at the ERI input to audio feedback circuit 25 indicates normal, beginning of life, battery energy. The battery status is voiced "BATTERY DEPLETED" if the ERI signal is generated by battery monitor 17 in response to detection of a depleted, end of life, battery energy. It should be noted that the medical care provider can leave the magnet 130 in place as shown in FIG. 1 or remove it at any time during the interrogation sequence described above. The emission of the voiced statements continues to completion even if the magnet is removed before all the voiced statements of the interrogation sequence are emitted. The "PACE" statement is suppressed at pacing pulses $P_4$ through $P_7$, for example, while these identification and status statements of the interrogation sequence are voiced. The "PACE" statements are voiced after the interrogation sequence is completed for as long as the magnet continues to be applied or until the predetermined count "n" is reached.

At time T3 in FIG. 3a, the magnet 130 is removed from the patient 102 in FIG. 1; and the MAGNET signal is no longer applied to the MAGNET input of audio feedback circuit 25. As shown in FIG. 3a, the audio feedback circuit 25 starts the internal event counter of ten PACE or SENSE events, for example, within which one or more re-applications of a magnetic field must be sensed by MAGFET 70 to continue with programming pacing rate, pulse width or amplitude. The sense amplifier 20 is no longer effectively disabled, and non-refractory sense signals pass through the AND gate 82 and reset the pacing escape interval being timed out in rate/TMT circuit 58. The termination of each escape interval by a non-refractory sense event or the time out of the escape interval is applied to the SENSE and PACE inputs of the audio feedback circuit 25 which counts them. The audio feedback circuit 25 continues to retrieve from memory and supply the ATD signals to the transducer 116 to emit the voiced statements "PACE" or "SENSE" on delivery of each pacing pulse, as at $P_{n+1}$ and $P_{N+10}$ and each SENSE signal at $S_{n+2}$ and $S_{n+3}$ shown in FIG. 3a. During this sequence, the medical care provider can use a stethoscope or the like to amplify and to hear the voiced PACE and SENSE statements and correlate them to a visual display of the same events. These voiced statements cease when a predetermined count of PACE and SENSE events accumulates in the event counter in the audio feedback circuit 25.

The illustration of FIG. 3a assumes that a magnetic field is not re-applied during the ten pace and sense events (counted by an event counter and supplied to logic block 78 on line 73) following time T3. FIG. 3b depicts a programming protocol sequence that is initiated by a single re-application of the permanent magnet that provides the MAGNET signal on line 80 during the above-described sequence after T3 but before the ten pace or sense events are counted. In this time period, the medical care provider or physician can listen to and count the number of voiced "PACE" and "SENSE" statements and time re-application of the magnet 130 to the patient's skin. The single re-application of the magnetic field within this ten event window is decoded in logic circuit 78 at the completion of the 10 event window to commence a pacing rate programming sequence in which base pacing rate is programmed.

FIG. 3c depicts a programming protocol sequence that is initiated by two re-applications of the permanent magnet that provides a signal N or S on line 72 or 74 during the above-described sequence after T3 but before the ten events are counted. The two re-applications of the magnetic field within the ten event count window is decoded in logic circuit 78 to commence a pacing pulse amplitude programming sequence in which pacing pulse amplitude is programmed. Similarly, three re-applications of the magnetic field within the ten event count window is decoded in logic circuit 78 to commence a pacing pulse width programming sequence in which pacing pulse width is programmed Programming any of these three programmable parameters is accomplished by first initiating the TMT and interrogation described above with reference to FIG. 3a. Then, after time T3, the appropriate number (one, two, or three) of magnet removal/replacement cycles must be performed within the ten event count window to switch logic circuit 78 into the programming mode for programming the desired parameter. This approach and the ability to hear the voiced "PACE" and "SENSE" statements makes it easy to reliably apply and remove the permanent magnet 130 from the patient's skin the required number of times after the initial removal of the permanent magnet 130 from the patient's skin at time T3 to select the desired parameter to re-program.

In the magnet removal/re-application cycles depicted in FIGS. 3b and 3c, it will be observed that the re-applied magnet 130 is held in place to provide the selected N-S or S-N magnetic field to the MAGFET 70 during the subsequent programming modes. Therefore, the continuously generated N or S signal is applied through the NOR gate 76 to one input of AND gate 82 to effectively disable the sense amplifier 20 and to commence pacing in the asynchronous mode. Pacing pulses are then delivered at the current programmed pacing rate, pacing pulse width and pulse amplitude. The logic circuit 78 decodes the applied number of removals and replacements of the magnet 130 and provides the corresponding programming mode control signals to the up/down control circuit 90 via lines 92.

Once in the decoded programming mode, up/down control circuit 90 adjusts the corresponding parameter value up or down, by an incremental amount at each asynchronous pacing cycle, depending upon the polarity of the detected magnetic field. For example, rate programming mode is initiated by completing the TMT and interrogation mode and then removing and replacing the magnet once as shown in FIG. 3b. The up/down control circuit 90 increases the pacing rate by an incremental amount (e.g. 5 PPM or 10 PPM) each pacing cycle so long as the N signal remains present on line 72, signifying detection of the N-S oriented magnetic field. Conversely, up/down control circuit 90 decreases the pacing rate by a like incremental amount each pacing cycle so long as the S signal is present on line 74, signifying the S-N oriented magnetic field. Programming the pacing rate to a desired level is thus accomplished by maintaining a S-N or N-S oriented magnetic field over MAGFET circuit 70 for enough pacing cycles to reach the desired level. When the desired rate is reached, rate programming is terminated by simply removing the magnet.

In the above-incorporated, commonly assigned '188 and '342 patents verification of the pacing rate change is effected by observing the delivery of redundant pacing pulses signifying the parameter being programmed by their number on the running EKG display. In the programming of rate, two such pacing pulses separated by 5 mSec are generated at the end of each pacing cycle as also shown in FIG. 3b. In the programming of pulse amplitude, three such pacing pulses separated by 5 mSec are generated at the end of each pacing cycle as also shown in FIG. 3c. Presumably, four such pacing pulses are generated at the end of each pacing cycle in order to signify that pacing pulse width is being programmed. The number of redundant pacing pulses show which parameter is being programmed but do not reveal the programmed parameter value. Mistakes in counting the pacing cycles can occur, and it is not easy to observe or measure incremental changes in these parameter values from the EKG tracing that is being printed or displayed on a video screen. It is necessary to know what the starting parameter value is and to mentally calculate the change from that value by counting the escape intervals until the end parameter value should be obtained. If the starting pacing pulse width or amplitude or pacing rate is not known and cannot be measured, then it may be necessary to follow the programming sequence to increase or decrease the programmed parameter value to its upper or lower limit. This upper or lower limit is reached by counting out the maximum number of escape intervals corresponding to the total number of possible incremental values. Then, the new parameter value is programmed by decrementing the parameter value from the maximum value or incrementing the parameter value from the minimum parameter value by the number sufficient to arrive at the desired programming value.

In accordance with a further feature of the present invention, the audio feedback circuit 25 and the audio transducer 116 are employed to generate and emit voiced statements of the programmed parameter value at the end of each escape interval. In this way, it is not necessary to employ the redundant and energy wasteful pacing pulses, and it is not necessary to calculate the correct number of pacing cycles required to make a correct change in the parameter value or to count the pacing cycles. This results in a simplified, more reliable, and less error prone programming function with benefits of reduced costs and improved patient safety.

Thus, in FIGS. 3b and 3c, the redundant pacing pulses employed in the above-incorporated, commonly assigned '188 and '342 patents are depicted, but it will be understood that they are not necessary in the practice of the present invention. Upon entering a programming mode via one, two or more removal/replacement cycles of the magnet, a voiced statement of the parameter that is being programmed, e.g., "Programming Rate" or "Programming Amplitude" is emitted.

Additionally, at each incremental change, the change in pacing rate, pulse width or pulse amplitude is voiced as depicted in FIGS. 3b and 3c. In this embodiment, particularly at high pacing rates, it may be necessary to make the incremental programmed changes and voice the changed value only at the end of every second or third or fourth escape interval to provide sufficient time for the complete phrase to be voiced. Or the phrase may be shortened to simply state the number for pacing rates which are multiples of either 5 or 10 and pulse widths which are stated in milliseconds. Additionally, ascending or descending scale musical tones can be emitted prior to or following each incremental increase or decrease, respectively, in the programmed parameter value to signify that the parameter value is being changed. As noted below, in certain IMDs one or more ascending or descending scale musical tone can be emitted following each increase or decrease in the parameter value, and the actual value need not be voiced in an emitted voice statement.

FIG. 4 sets forth an exemplary list of pacing rates, pulse widths and pulse amplitudes that are voiced in the programming modes and that are coded to memory addresses of the analog storage array described below with reference to FIG. 6. For example, voiced statements of pulse widths in a range of 0.1 mSec to 1.0 mSec at 0.1 mSec increments and pacing rates between 50 PPM and 100 PPM at 5 PPM increments are stored in memory. Voiced statements of pacing pulse amplitudes "AMPLITUDE LOW", "AMPLITUDE MEDIUM" and "AMPLITUDE HIGH" for three programmable amplitudes, for example, are also stored in memory.

Figure 5:
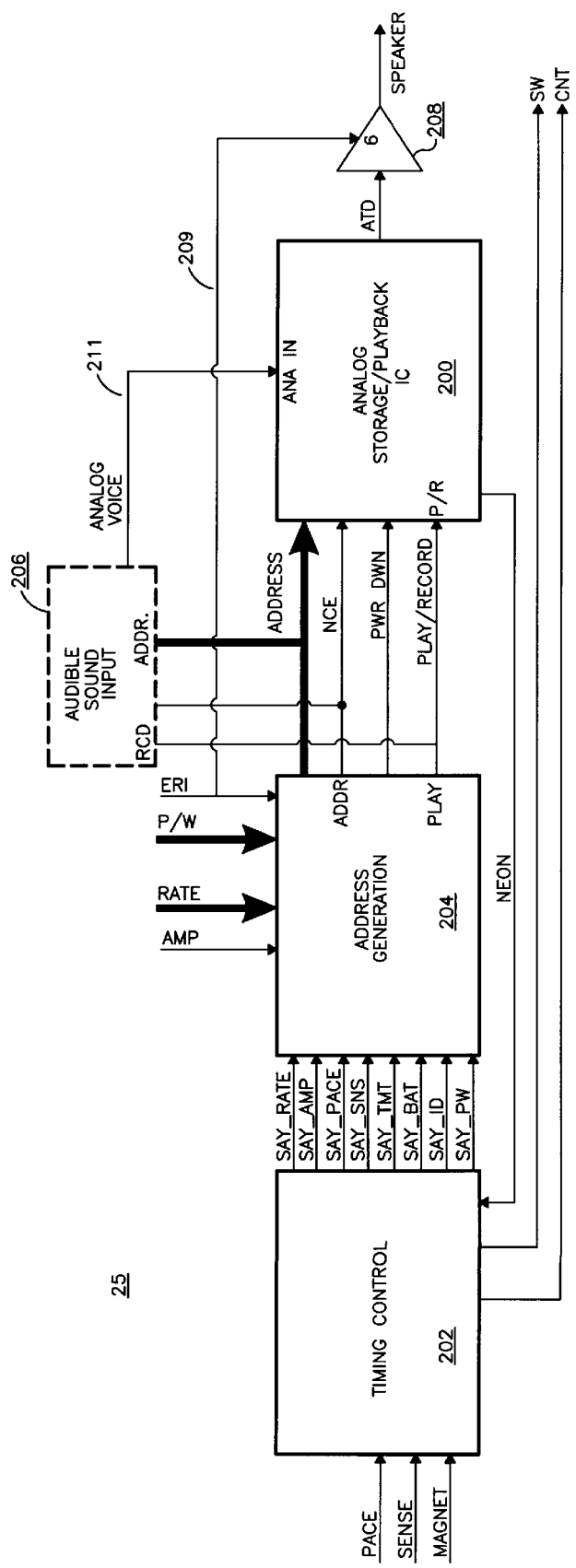
FIG. 5 is an expanded block diagram of the audio feedback circuit block of FIG. 2 illustrating how the transducer drive signals that drive the audio transducer to emit the voiced statements shown in the interrogation and programming sequences illustrated in FIGS. 3a–3c are generated.

FIG. 5 is an expanded block diagram of the audio feedback circuit 25 of FIG. 2 and includes an analog storage/playback IC 200, timing control logic circuit 202 and address generation logic circuit 204. In addition, a sound input block 206 is depicted in broken lines to illustrate storage of analog voiced statements and/or musical tones in analog memory in the analog storage/playback IC 200, which typically takes place in the course of manufacturing the pacemaker IPG or other IMD as explained below. In other embodiments, such recording may take place after manufacture of the pacemaker IPG is completed in a manner described below. The analog storage/playback IC 200 is preferably one of the ISD2500 Series, ChipCorder® single-chip voice record/playback devices sold by Information Storage Devices, Inc. (ISD) located in Los Alton Hills, Calif., and particularly, the model ISD2560 depicted in FIG. 6. Such analog storage/playback ICs are disclosed in U.S. Pat. No. 4,890,259, incorporated herein by reference, and other related ISD patents.

In FIG. 5, the timing control circuit 202 is interconnected with the IPG circuit to receive the PACE trigger pulse on line 64, the SENSE event signal on line 48, and a MAGNET signal on line 80 whenever the N (UP) or S (DOWN) signal is present on lines 72 and 74, respectively. Timing control circuit 202 establishes the protocols depicted in FIGS. 3a–3c and described above and generates the commands that are applied to the address generation circuit 204 depicted in FIG. 5. These commands are generated particularly during the TMT mode, the asynchronous interrogation mode, and the subsequent normal operating mode depicted in FIG. 3a. The address generation circuit 204 also receives the ERI signal from battery monitor 17 on line 23 and the pulse amplitude (AMP), the pacing rate (RATE), and the pulse width (PW) programmed operating parameter values from up/down control circuit 90 on lines 91, 93 and 95, respectively. During the asynchronous interrogation mode of FIG. 3a, the AMP, RATE and PW programmed parameters and the ERI signal are converted to the memory addresses listed in FIG. 4 for the programmed values and battery condition. These commands prompt the address generation circuit 204 to select and apply the memory addresses for the voiced statements identified above and listed in FIG. 4 to the ADDRESS input line to the analog storage/playback IC 200.

Figure 7:
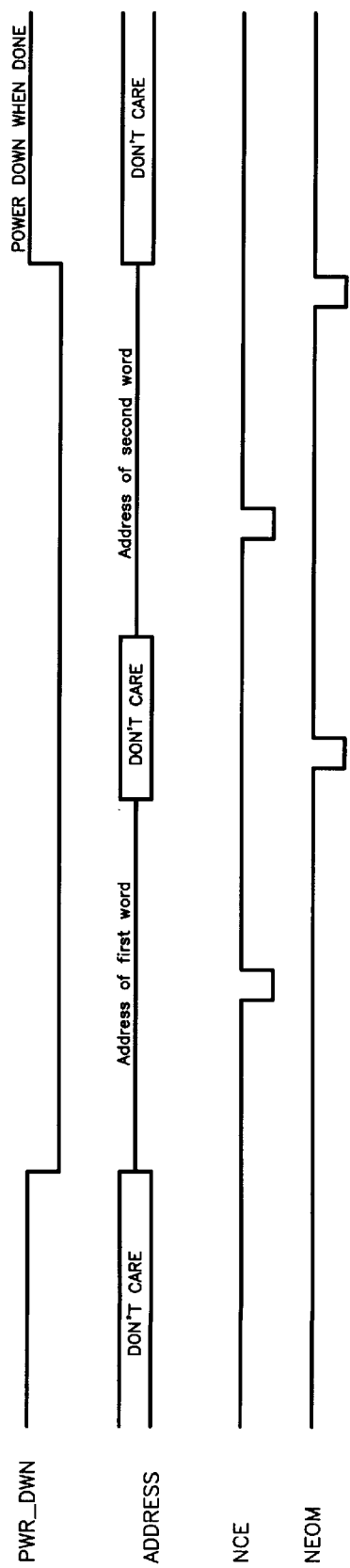
FIG. 7 is a timing diagram depicting the generation of a two word message in the block diagram of FIG. 5.

It would be possible to combine voiced statements retrieved in tandem from two memory addresses to form a voiced phrase as shown in FIG. 7. For example, the PACE signal and the programmed pacing RATE value can be employed to select the addresses in tandem to voice a "PACE XX PPM" phrase from the "PACE" statement and the "XX PPM" rate statements depicted at two addresses in FIG. 4 (where "XX" is the presently programmed value).

During the programming modes illustrated in FIGS. 3b and 3c, the increased or decreased AMP, RATE and PW programmed parameter values are similarly converted to the memory addresses listed in FIG. 4 and applied to the ADDRESS input of the analog storage/playback IC 200.

The address generation circuit 204 also supplies the "not chip enable" (NCE) command and the PLAY command to the analog storage/playback IC 200 in order to start or trigger playback at the addresses supplied to the ADDRESS bus. The voice that is addressed is supplied to playback filter and amplification stages and supplied to the SPKR output coupled through electronic switch 31 to the audio transducer 116. When the voiced statement is completed the logic level on the "not end of message" (NEOM) line switches to alert the timing control 202 to queue up the next voice command to the address generation block 204. The above-described sequence of voiced statements of device identification, operating conditions and mode or states and programmed parameter values are sequentially generated in the interrogation mode by the "hand shake" cooperation between timing control 202 and analog storage/playback IC 200. Similarly, each device operation, i.e., PACE trigger pulse or SENSE event signal causes the timing control 202 to instruct the address generation circuit 204 to supply the address for the voiced "PACE or "SENSE" statement to the ADDRESS input of the analog storage/playback IC 200. The address generation circuit 204 also supplies the "power down" (PWR_DWN) logic level to the analog storage/playback IC 200 in order to place the analog storage/playback IC 200 in a "zero power" mode when not in use.

The sound input block 206 is used to record voiced statements and/or musical tones through line 211 at predetermined addresses in analog storage/playback IC 200. The sound input block 206 supplies the addresses and provides a record command signal on play/record line and the not chip enable (NCE) signal on the NCE line. The NCE input receives an enable logic level to commence recording of the voiced statement (or musical tone) that is addressed on the ADDRESS bus. FIG. 5 also includes an additional circuit to operate the audio transducer in a high volume mode to generate a warning to the patient of device malfunction and imminent delivery of a therapy, where appropriate. A variable gain audio amplifier 208 is provided that is increased in gain by application of a gain control signal on line 209 when a specific voiced statement is to be emitted at a volume that can be heard by the patient. In FIG. 5, the specific, high volume, voiced statement "BATTERY DEPLETED" or the equivalent is emitted periodically if the ERI signal is generated by battery monitor 17 in response to detection of a depleted, end of life, battery energy as described above. In this case, the ERI signal on line 209 provides the gain control signal to trigger the gain increase of variable gain audio amplifier 208 as long as it is present. Voiced statements can also be stored and emitted advising the patient to contact his/her physician or medical care provider. A timer is employed in the address generation block that responds to the ERI signal and periodically enables the generation of the address of this warning to the patient, e.g., once every hour, so that it is not continually generated. The ERI function and/or the gain of the variable gain amplifier can be automatically set low when an interrogation or programming sequence is conducted in accordance with FIGS. 3a–3c to allow those functions to be completed. Moreover, in more complex, multi-programmable embodiments than illustrated in FIG. 2, this function can be programmed on or off by the medical care provider employing the programmer to emit the appropriate programmed command.

Figure 6:
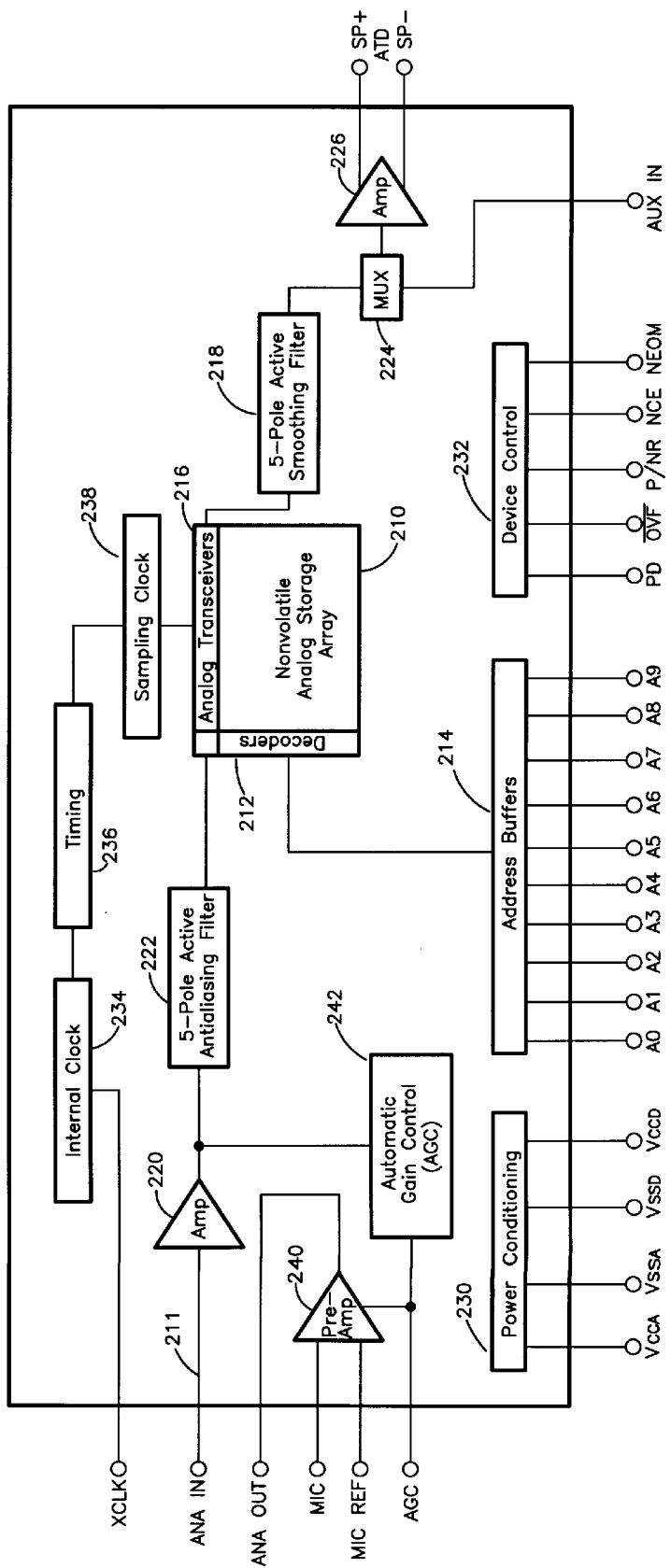
FIG. 6 is a block diagram of the analog storage/playback IC of FIG. 5.

FIG. 6 is a simplified block diagram of the analog storage/playback IC 200, and it includes components for recording voiced statements in a non-volatile analog storage array 210 and playing back the voiced statements via analog speaker outputs SP+ and SP− coupled to the audio transducer 116 through electronic switch 31. The ISD2560 ChipCorder® analog storage/playback IC 200 is a CMOS device that operates at 3 volts and provides playback of 60 seconds of analog voice recordings stored in non-volatile analog storage array 210. The analog voice recordings are addressed via decoders 212 coupled to the ADDRESS buffers 214 and applied to the analog output amplifier 226 as described below. The analog storage array is a multilevel storage, EEPROM array that is proprietary to ISD and is described in detail in the above-incorporated ISD '259 patent.

The CMOS device includes power conditioning circuit 230 that is intended to be coupled to external components forming a regulated power supply coupled with the power source 11 for supplying power to the other depicted circuits. A device control circuit 232 is also coupled with the other depicted circuits and governs device operations depending on the intended application. In accordance with the present invention, the PWR_DWN signal from the address generation block 204 is applied to the PD input to device control circuit to enter the zero power mode to minimize battery drain at all times other than during voice recording or playback. It is alleged that audio or voiced statements stored in non-volatile analog storage array 210 can be retained 100 years without consuming any power. A PLAY or RECORD logic level is applied to the P/NR input during playback or recording of voiced statements. The NCE input receives an enable logic level to commence recording the voiced statements in memory at the specified address of the playback of the voiced statement that is addressed on the ADDRESS bus. A NEOM logic level signal is outputted from the device control circuit 232 and applied to the timing control 202 when the voiced statement or phrase is completed in order to allow the next voiced statement or phrase to be addressed as noted above.

An on-chip oscillator is provided by the internal clock 234 that can be also driven by external clock signal XCLK (not employed in the practice of the present invention). The internal clock 234 provides clock signals to internal timing circuit 236 which provides a sampling frequency to sampling clock 238 and to the 5-pole active anti-aliasing filter 222 and to the 5-pole active smoothing filter 218.

The audio or voice recording section of the CMOS device includes the speech or audio input amplifier 220 for amplifying the audio input signal at ANA IN and applying the amplified signal coupled to anti-aliasing filter 222. The filtered input signal is sampled by sampling clock 238 and the sampled analog values are stored directly into memory cells through analog transceivers 216 for later retrieval when addressed via decoders 212. The manner of storage and the assignment of addresses is described in the above-incorporated ISD 259 patent. A further pre-amplifier 240 and AGC circuit 242 are provided on the IC but are not employed in the practice of the present invention.

In accordance with one feature of the present invention, the voiced statements are recorded in a particular human language at completion of manufacture of the pacemaker IPG circuit 10 (or other IMD circuit), but before the circuit 10 is enclosed in the IPG housing. Alternatively, the voiced statement recordings are supplied to the vendor, ISD in this instance, and recorded in the analog storage array 210 before the analog storage/playback IC 200 is delivered. In another alternative approach, the pacemaker IPG or other IMD could be provided with a feedthrough for direct coupling with the ANA IN terminal of amplifier 220 for recording the voiced statements in the manner described in the above-incorporated, commonly assigned '096 patent. In this variation, it would be possible for a distributor or a physician implanting the medical device in a given country or region to employ the local language in storing the voiced statements. In accordance with a further aspect of the present invention, musical tones can also be recorded through audio input amplifier 220 at certain memory locations for use in conjunction with voiced statements.

In accordance with another feature of the present invention, the voiced statements can be recorded in more than one language, and the medical care provider or physician can select the language to be used. In more sophisticated IMDs having RF telemetry capabilities, the specific language can be selected by a downlink RF telemetry command. In the low cost pacemaker IPG 10 described above, a further repeated sequence of successive removals and replacements of magnet 130 within the specified time period, can be detected by appropriate circuitry in logic circuit 78 and applied to address generation circuit 204 to select a language to be used.

Regardless of how the voiced statements are recorded in analog storage array 210, the analog voice samples of the voiced statements are sequentially retrieved from storage locations in the analog storage array 210 when they are addressed via decoders 212. The analog voice samples are sequentially retrieved through the analog transceivers 216 at the sampling clock frequency and applied to the 5-pole active smoothing filter 218 to recompose the words of the phrase in a natural cadence and speech form. The reconstituted voiced statements pass through the multiplexor 224 and are applied to the input terminals of the output amplifier 226 where they are amplified and output at output terminals SP+ and SP–. The auxiliary input to multiplexor 224 is not employed in the present invention.

It will be understood that this preferred embodiment of the invention may be modified to provide differing programming and interrogation sequences. The MEDTRONIC® Champion™ single chamber, pacemaker IPG system shares a similar architecture and operating system as the preferred embodiment described above but is programmed by successive magnet removals and re-applications and indicates programmed operating modes and parameters in a somewhat different manner. The system includes the MEDTRONIC® Model 9710 programmer which only detects and displays pacing intervals on a display to facilitate ECG interpretation using the method described in commonly assigned U.S. Pat. No. 4,226,245 to Bennett, incorporated herein by reference. Even when the intervals are displayed, it is difficult to program the pacing rate while viewing and interpreting the pacing interval display in order to count pacing intervals and synchronize the generation of the programming command to counted intervals. This method is prolonged and subject to error. The present invention may be implemented into the Champion™ systems to provide voiced statements during an interrogation sequence and voiced "PACE" and "SENSE" statements to aide in understanding the TMT operation and to time re-programming.

In the Champion™ IPG, the programmed pacing rate is reduced by a measurable percentage in response to an ERI signal so that the medical care provider can observe the current rate and interpret that the battery is depleted from that observed pacing rate. For example, the programmed pacing rate of 75 PPM may be reduced to 58 PPM when the battery voltage falls below an ERI threshold voltage. A reed switch is included in addition to the MAGFET that is closed by an applied magnetic field to commence an interrogation sequence that culminates in a TMT after the magnet is removed rather than commencing with the TMT sequence. The applied magnet closes the reed switch and causes the pacing mode to change to the asynchronous mode and the programmed pacing rate to be restored in an initial sequence of 3–4 asynchronous pacing pulses. Then, the asynchronous pacing rate changes to the ERI rate, if the battery voltage is below the ERI threshold, or remains at the programmed pacing rate for a second sequence of asynchronous pacing pulses. The medical care provider observes the pacing artifacts on an ECG display and compares the observed escape intervals to determine whether there is an apparent difference and draws a conclusion that the battery voltage is or is not depleted requiring replacement of the IPG. The magnet is then removed, and the pacing mode returns to the inhibited mode at a preset escape interval corresponding to 75 PPM, for example, and a fixed number of pacing escape intervals are counted in a third sequence. The TMT sequence of four asynchronous pacing pulses at an elevated pacing rate and a programming window sequence including the TMT sequence and seven more pacing pulses are commenced at the end of that count. Again, the medical care provider observes the ECG display to determine if the reduced energy pacing pulse of the TMT sequence captures the heart.

In this embodiment of the present invention, the voiced statements of the interrogation mode of FIG. 3a, including the battery status, can be commenced and completed in the initial sequence of fixed rate pacing pulses at the programmed pacing rate. The second sequence could be augmented by voiced "PACE XX PPM" statements (where "XX" is the presently programmed value) emitted synchronously with each PACE trigger. Similarly, the pacing pulses of the TMT sequence could be augmented by voiced "PACE" and "TMT PACE" statements, and the pacing pulses of the programming window sequence could be augmented by voiced "PACE" and "SENSE" statements.

Only the pacing rate and pacing pulse amplitude are programmable in the Champion™ pacemaker IPG. In the programming sequences of the Champion™ pacemaker IPG, the N-S and S-N magnetic fields are used to program the pacing rate and pulse width, respectively. The programmed parameter value is incremented when the magnetic field is quickly applied and removed twice in rapid succession in an increment window between three successive pacing pulses. The programmed parameter value is decremented when the magnetic field is quickly applied and removed once. In either case, it is necessary to wait until three escape intervals lapse with PACE trigger pulses before the parameter value can be again incremented or decremented. Once a desired parameter value is achieved, no more magnetic fields are applied, and the pacing mode reverts to the inhibited pacing mode after ten pacing pulses are delivered from the last application of a magnetic field.

In this embodiment, the present invention can be implemented to voice "PACE" statements and thereby assist in timing the application(s) of the magnetic fields sufficiently far apart and within the increment window to avoid misprogramming. The voiced "PACE" statements can augment the delivery of the final ten pacing pulses.

The above-described embodiments of the pacemaker IPG are implemented in custom integrated circuits incorporating the analog storage IC 200. This same approach can be used for a number of other IMDs, e.g. electrical stimulators of the type disclosed in commonly assigned U.S. Pat. No. 4,520,825 to Thompson et al., incorporated herein by reference.

The invention can also be incorporated into more sophisticated, micro-computer based IMDs identified below in reference to FIG. 10.

Figure 8:
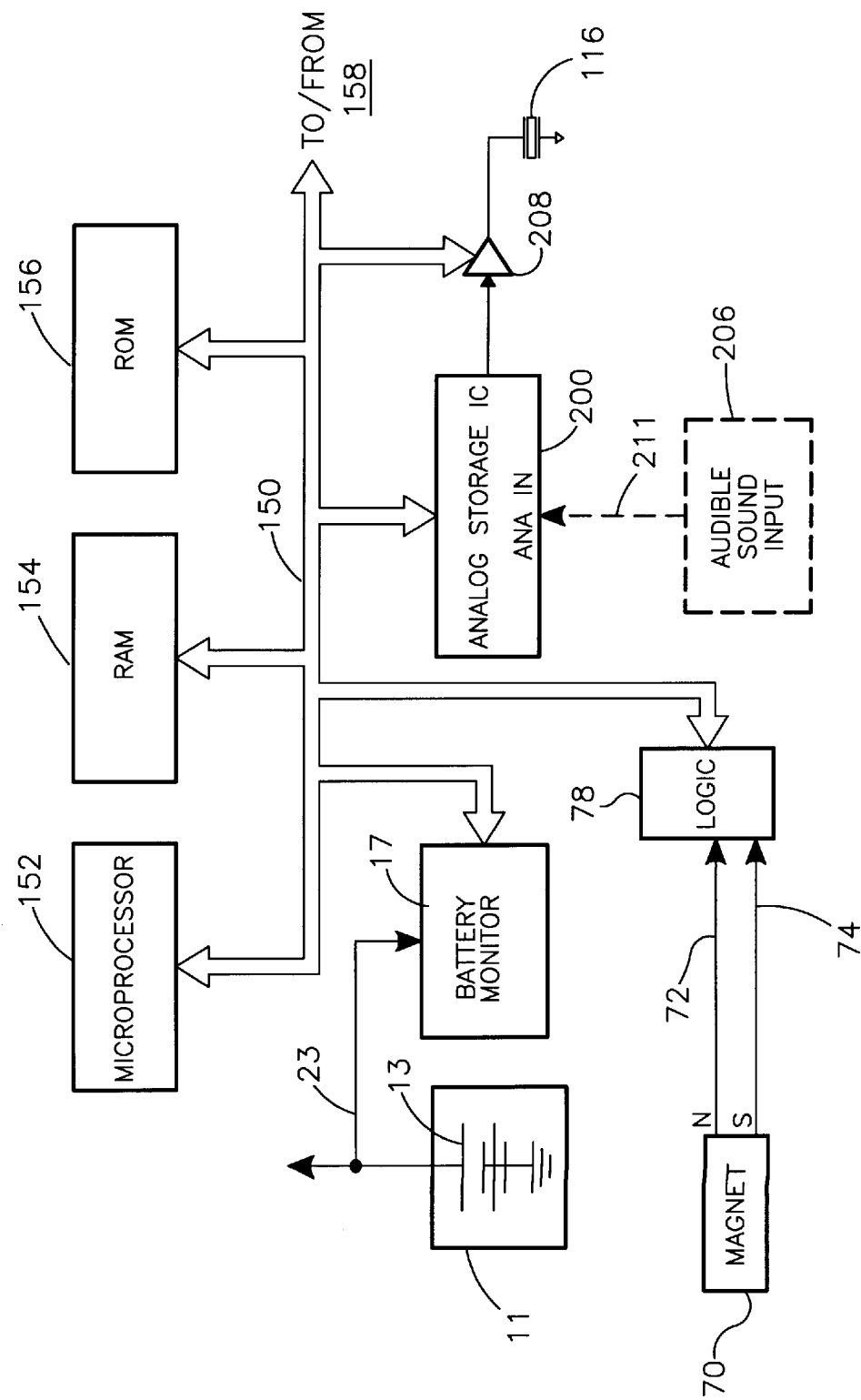
FIG. 8 is a block diagram of a microcomputer based IMD operating system intended to be used in conjunction with a controller and monitor or therapy delivery system of one of the types depicted in FIG. 10 that is capable of being interrogated or programmed by successive applications of a magnetic field.
Figure 9:
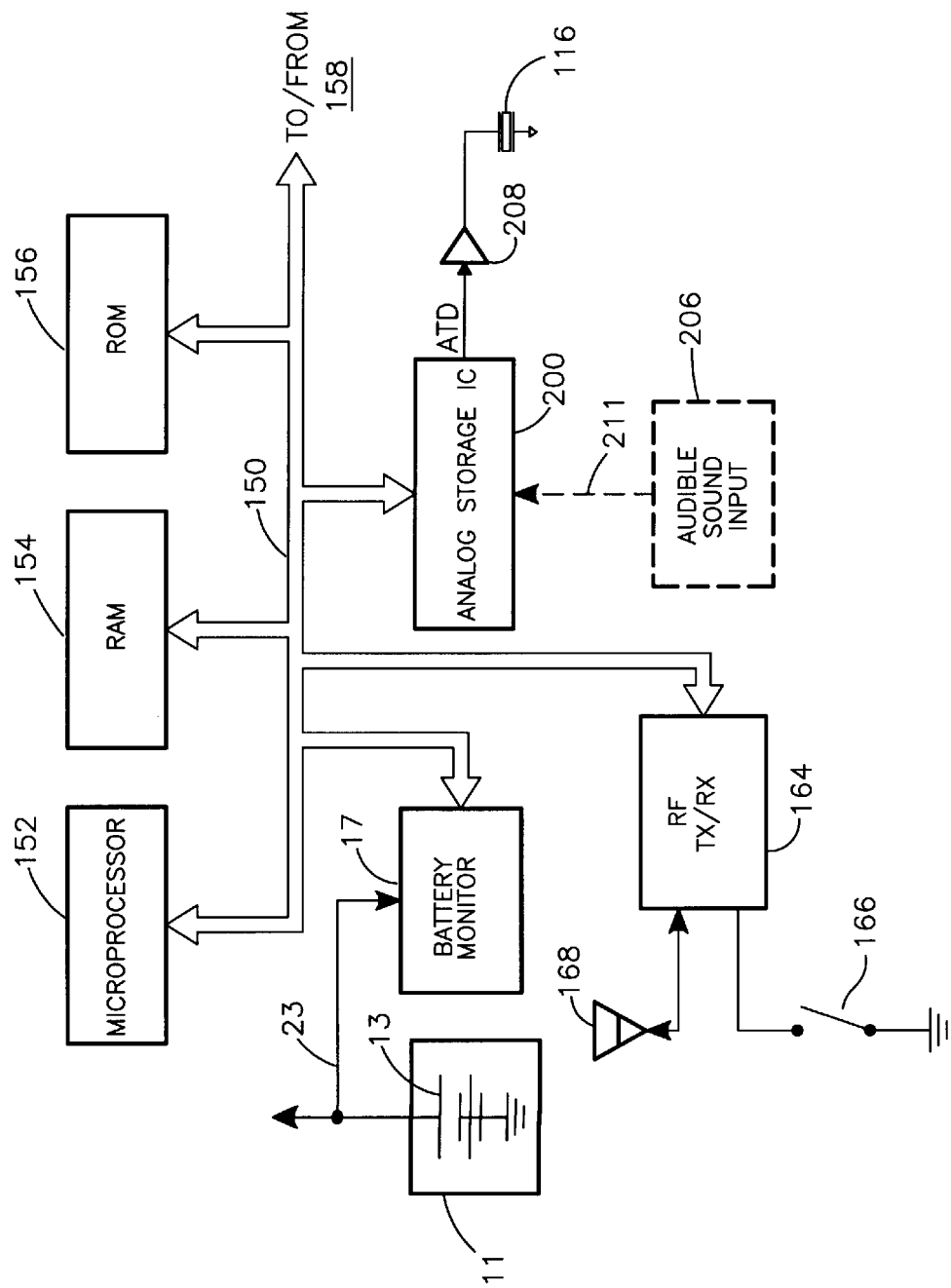
FIG. 9 is a block diagram of a microcomputer based IMD operating system intended to be used in conjunction with a controller and monitor or therapy delivery system of one of the types depicted in FIG. 10 that is capable of being interrogated or programmed using an RF telemetry transmission system.
Figure 10:
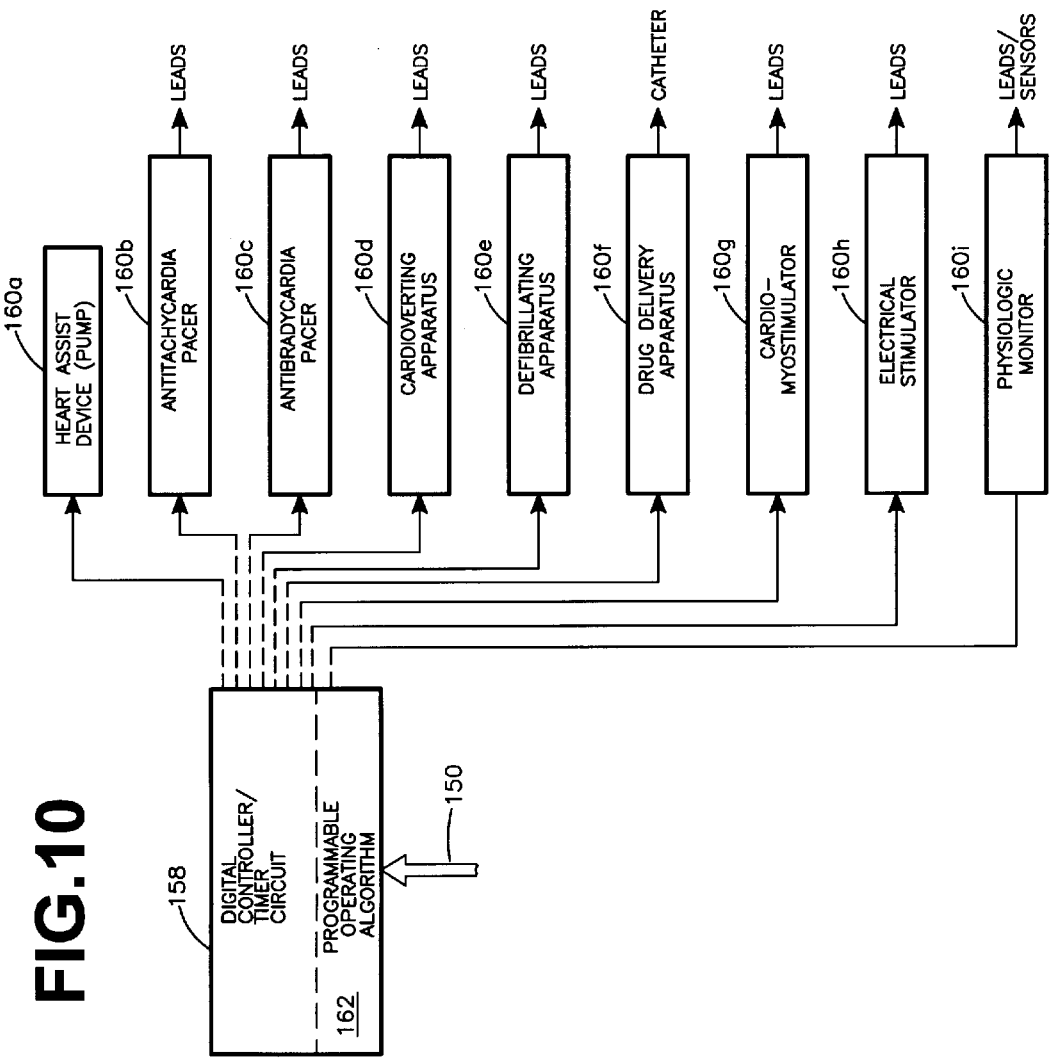
FIG. 10 is a block diagram of a digital controller/timer circuit usable with the operating systems of FIGS. 8 or 9 and with one of the depicted monitors and therapy delivery devices

FIGS. 8 and 9 are block diagrams of such microcomputer based IMD operating system intended to be used in conjunction with a controller and monitor or therapy delivery system of one of the types depicted in FIG. 10. The micro-computer based system of FIGS. 8 and 9 comprises a microprocessor 152 coupled by a data and command bus 150 with RAM 154, ROM 156, analog storage/playback IC 200, audio amplifier 208, the battery monitor 17 and the digital controller/timer circuit 158 of FIG. 10. The digital controller/timer circuit 158 which is coupled with a specific monitor or therapy delivery system 160a–160i. Other components or circuit blocks that are used in a specific IMD may also be connected with the data and control bus 150.

The analog storage/playback IC 200 is configured as described above in reference to FIG. 6. Audio transducer drive signals for emitting voiced statements or musical tones are stored in the analog storage array 210 of FIG. 6 using the sound input block 206 and associated signals in the manner described above. The sound input block 206 may not be present in the IMD or may be disabled if the ATD signals are recorded during manufacture of the IMD and no option is provided to allow recording by a distributor or physician. If the sound input block 206 is present and enabled, it would be coupled with the data and control bus 150 to allow its usage particularly in the embodiment of FIG. 9 where appropriate commands could be received in a downlink telemetry transmission.

In these embodiments, it is not necessary to employ the timing control circuit 202 or the address generation circuit 204 of FIG. 5 to control the operation of the analog storage/playback IC 200. In this micro-computer based operating system, the timing of operations of the analog storage/playback IC 200 as described above are governed by interrogation and programming algorithms stored in ROM 156 and enabled by microprocessor 152. The memory location addresses for the ATD signals stored in the analog storage array 210 are also stored in ROM 156 and selectively retrieved and applied to the address buffers 214 in accordance with the interrogation and programming algorithm.

The IMD of FIGS. 8 or 9 in conjunction with FIG. 10 is powered by the battery 13 in the power source 11, and battery voltage is monitored by the battery monitor 17. The battery voltage is either encoded in battery monitor 17 and supplied to data and command bus 150 or an ERI warning trigger signal is developed in the battery monitor 17 in the manner described above and encoded and supplied to data and command bus 150 to the microprocessor 152. During an interrogation sequence, the battery voltage itself or a simplified voiced statement that the battery voltage is "OK" or "depleted" is emitted by audio transducer 116 as described above.

At other times, if the encoded battery data signifies that the battery 13 is depleted to an ERI voltage, the microprocessor 152 commences a warning routine to cause the audio transducer 116 to emit a warning voiced statement or musical tone at an audible volume that the patient can hear. During the warning routine, the microprocessor periodically (e.g., once every hour) retrieves the address of the appropriate ATD signal and directs it on data and control bus 150 to the address buffers 214 of analog storage/playback IC 200. The NCE and NEOM commands are also applied on data and control bus 150, and a high gain signal is applied to the gain input of the variable gain audio amplifier 208.

The variable gain audio amplifier 208 amplifies the ATD signal and applies it to the audio transducer 116 to emit the high volume, battery ERI warning.

Other warning routines may also be included in the microcomputer based operating system for providing such high volume, audible sound warnings to the patient when a triggering event occurs. The triggering event can include certain operations of the IMD or other changed conditions or states of the IMD. For example, in the context of an implantable drug delivery system, the patient can be warned that the medication supply is depleted. In the context of an implantable cardiac monitor or cardioverter/defibrillator, the patient can be warned that an arrhythmia has been detected by the arrhythmia detection algorithm and to take appropriate action. The onset of the malignant condition of the patient is detected, and the warning trigger signal is generated in response to the detection. The patient is warned to seek medical assistance or take other precautions by emission of the audible signal. In the case of a cardioverter/defibrillator, the patient can be advised to get in a resting position before the cardioversion/defibrillation shock is delivered.

In each case, the triggering event causes the microprocessor to retrieve and apply the commands for operating the analog storage/playback IC 200 and the variable gain audio amplifier 208 and the addresses of the appropriate ATD signal. The analog storage/playback IC 200 retrieves the addressed ATD signal and applies it to the variable gain audio amplifier 208, and the audio transducer 116 emits the voiced statement or musical tone warning to the patient.

In FIG. 8, an interrogation and programming system responsive to successive applications of a magnetic field to a MAGFET 70 is illustrated for interrogating IMD information and for programming device operating modes and parameter values. The MAGFET 70 detects the polarity of the applied magnetic field and generates the corresponding N and S signals on lines 72 and 74, respectively, in the manner described above in reference to FIG. 2. The N and S signals are applied to logic circuit 78, and logic circuit 78 develops an appropriate encoded signal that is applied on data and control bus 150 to microprocessor 152 to initiate the programming or interrogation algorithm. Thus, a communication session is established by applying the magnet 130 to the patients skin as shown in FIG. 1 and described. The magnetic field constitutes a communication link signal that is detected by the MAGFET 70 to establish the communication session.

In FIG. 9, the communication session is established using an RF telemetry transmission based, programming and interrogation system for interrogating IMD information and for programming device operating modes and parameter values. The programming head (not shown) of the programmer (not shown) typically includes a permanent magnet that closes reed switch 166 and generates downlink RF telemetry signals that are received by the RF telemetry antenna 168 and applied to the RF telemetry transmitter/receiver circuit 164. The received downlink RF telemetry signals are decoded by the RF telemetry transmitter/receiver circuit 164 and then encoded for transmission on data and control bus 150 and constitute communication link signals. Uplink RF telemetry transmissions of IMD information received on data and control bus 150 are generated in the RF telemetry transmitter/receiver circuit 164 and applied to RF telemetry antenna 168 in an uplink telemetry transmission routine. The microprocessor 152 commences an uplink RF telemetry transmission routine and supplies data and control signals on data and control bus 150 to RF telemetry transmitter/receiver circuit 164.

The system of FIG. 9 can be configured in many different ways to share the uplink communication capabilities of the audible sounds generated by the audio transducer 116 with the RF telemetry uplink transmissions. In a simple application, the RF telemetry transmission system can be used to receive programming and interrogation commands, and the interrogated data and programming confirmation can be transmitted by audible sounds. At the opposite extreme, only limited IMD information can be provided through emission of audible sounds.

In the system of FIG. 8, the patient can be provided with a magnet to program limited operating modes or parameter values and received audible sound feedback confirming such programming or to interrogate certain IMD information. It will be understood that the interrogation and programming system of FIG. 8 can be included in the operating system of FIG. 9 to allow the patient to use the magnet for the same purpose. Or the patient can be provided with a limited function programmer for RF telemetry downlink transmission of limited interrogation and programming commands that are responded to by the audible sound emission of the corresponding IMD information.

In this regard, the high volume, audible sound emission capability can also be employed during programming or interrogation routines that the patient is allowed to self initiate. For example, if the patient is supplied with a limited programmer or magnet for increasing or decreasing dosage of a drug or a symptom alleviating electrical stimulation, the programmed change can be confirmed by emission of an audible voiced statement or musical tone. In each case, the programmed change causes the microprocessor to retrieve and apply the commands for operating the analog storage/playback IC 200 and the variable gain audio amplifier 208 and the addresses of the appropriate ATD signal. The analog storage/playback IC 200 retrieves the addressed ATD signal and applies it to the variable gain audio amplifier 208, and the audio transducer 116 emits the voiced statement or musical tone confirming the change to the patient. Examples are described below in reference to FIGS. 11 and 12.

FIG. 10 is a block diagram of a digital controller/timer circuit 158 usable with the operating systems of FIGS. 8 or 9 and with a therapy delivery device 160a–160h or physiologic monitor 160i. It will be understood that many of the identified therapy delivery devices 160a–160h also have monitoring capabilities that accumulate physiologic data for later interrogation. It will be understood that the logic 78 and the RF telemetry transmitter/receiver 164 of FIGS. 8 and 9 can be incorporated within the digital controller/timer circuit 158 in any particular therapy delivery device and monitoring configuration. In each IMD configuration case, the digital controller/timer circuit 158 and the appropriate programmable operating algorithm 162 govern all operating functions.

With respect to therapy delivery device configurations, the IMD may be configured to operate an implantable heart assist device or pump 160a implanted in patients awaiting a heart transplant operation. In this case, the derived relative blood pressure and/or temperature values may be used to modulate the action of the pump to maintain adequate cardiac output. Or it may be configured to include any one or a combination of the anti-tachycardia pacer 160b, anti-bradycardia pacer 160c, cardioverting apparatus 160d and/or defibrillating apparatus 160e having suitable leads and electrodes extending from the implantable therapy delivery medical device 100 to the patient's heart 10 for sensing the electrogram (EGM) and delivering pacing pulses or cardioversion/defibrillation shocks. The IMD may be configured to include the drug delivery apparatus 160f which is coupled to a suitable catheter extending to the patient's heart 10 or vascular system to directly deliver drugs to treat hypertension, for example. The IMD may be configured as a MEDTRONIC® Transform™ Cardiomyostimulator 160g having suitable leads extending to the patient's heart and the skeletal muscle wrapped about the heart to sense the cardiac EGM and time delivery of the muscle stimulation pulses. Again, the derived relative blood pressure and/or temperature values may be used to modulate the muscle stimulation rate to maintain adequate cardiac output. The IMD may also be configured as an electrical stimulator 160h, including nerve and muscle stimulators, deep brain stimulators, and cochlear implants, for applying electrical stimulation therapies to electrodes sited at appropriate locations of the patient's body.

Finally, the IMD can also be configured as an implantable monitoring system for monitoring physiologic conditions, e.g., a cardiac monitor for monitoring the patient's heart EGM and/or for monitoring blood pressure, temperature and blood gas or pH. The MEDTRONIC® Reveal™ implantable loop recorder records a 42 minute segment of EGM when the patient feels the effects of an arrhythmic episode and activates the recording function by applying a magnet over the site of implantation. The MEDTRONIC® Chronicle™ implantable hemodynamic recorder employs the leads and circuitry disclosed in commonly assigned U.S. Pat. Nos. 5,535,752 and 5,564,434, incorporated by reference herein, to record the EGM and absolute blood pressure values for predetermined time intervals.

A wide variety of IMD information can be conveyed in any of these therapy delivery or monitoring systems by way of audible voiced statements or musical tones stored in the analog storage array 210 of the analog storage/playback IC 200. Two specific examples are set forth in FIGS. 11 and 12 that show how the present invention can be employed to simplify interrogation and programming of IMDs that typically provide for limited function programming by the patient to relieve symptoms felt by the patient.

In these embodiment, the patient is typically supplied with a patient activator or programmer to turn a therapy on or off and/or to increase or decrease a therapy parameter. Specifically, the above-referenced MEDTRONIC® Itrel® implantable nerve stimulator and Synchromed® drug infusion system are provided with such patient activators to allow the patient to adjust the stimulation and drug therapies to relieve pain symptoms. In accordance with the following described embodiments of the present invention, musical tones are emitted by the IMD when it is programmed by the patient to adjust the stimulation and drug therapies using such a patient activator or a magnet. A series of ascending scale musical tones can be emitted upon delivery of an increased stimulation energy or medicinal bolus therapy in response to use of the patient activator or magnet. Similarly, a series of descending scale musical tones can be emitted upon delivery of an decreased stimulation energy or medicinal bolus therapy in response to use of the patient activator or magnet. Moreover, the programmed stimulation energy or bolus volume can also be voiced in accompaniment with the ascending or descending scale musical tones or chimes.

FIG. 11 is a chart depicting the memory address locations of ATD signals for emitting voiced statements or musical tones in interrogation and programming sequences of an implantable drug delivery apparatus 160f of FIG. 10 having an operating system of FIG. 8 or FIG. 9. The chart of FIG. 11 depicts the memory address locations for emitting voiced statements or musical tones in an interrogation sequence of current IMD information at analog memory addresses "00"–"0D" followed by a programming sequence for increasing or decreasing a drug infusion rate at addresses "0E" and "0F". In the interrogation and programming sequences, the medical care provider can commence the interrogation using either a programmer in the case of a configuration using the operating system of FIG. 9 or a magnet 130 in the case of a configuration using the operating system of FIG. 8.

Assuming the latter case and assuming that the IMD 100 of FIG. 1 is a drug delivery system incorporating the drug delivery apparatus 160f, the medical care provider applies the magnet 130 over the MAGFET 70 which produces either the N or S signal on line 72 or 74 of FIG. 8. The logic circuit 78 responds by providing an interrupt to the microprocessor 152 to commence the interrogation routine. The analog memory address "01" is provided on bus 150 to analog storage/playback IC 200 which emits the voiced statement "Data Start" or a musical tone at an identifiable audible frequency. Then, the interrogation routine sequentially selects the programmed one of the addresses "02"–"05" for the current infusion rate, "06"–"0A" for the remaining drug quantity, and "0B" or "0C" for the battery condition. The ATD signals cause the emission of voiced statements in these cases. Then, the "End Data" statement or a further musical tone at the same or a different frequency than the "Data Start" frequency is emitted by providing address "0D" on bus 150 to the analog storage/playback IC 200. In the illustration of FIG. 1, these statements are emitted at a volume that is not audible to the patient 102 but can be heard by the medical care provider using the stethoscope 142 or a simple audio amplifier.

During the interrogation sequence, the battery voltage is monitored and the appropriate one of the addresses "0B" or "0C" are provided to the analog storage/playback IC 200 at the specified point in the sequence. The detection of the magnet 130 causes the microprocessor 152 to suspend the periodic emission of the battery depletion warning that would take place at other times if the battery 13 is depleted to the ERI voltage. Similarly, the detection of the magnet 130 causes the microprocessor 152 to suspend the periodic emission of the drug depletion warning that would take place at other times if the drug quantity is depleted to the "Less than 2 days remaining" or a lower quantity. However, it will be understood that during the normal operation, these voiced statement or musical tone warnings at addresses "0A" and "0C" are emitted at a volume that can be heard by the patient as described above.

The magnet 130 can be withdrawn to end the interrogation sequence or it can be left in place or rotated end to end to commence the programming sequence to increase or decrease the rate of delivery of the drug. In either case, the programming sequence commences with a rate increasing mode by providing the address "0F" to cause the emission of the "rate increasing" voiced statement or the ascending scale musical tone. Then, within the time of a few seconds, the medical care giver can either leave the magnet 130 in place to continue in the rate increasing mode or reverse it end to end to cause the programming sequence to switch to a rate decreasing mode. In the former case, after a few seconds, the rate is incrementally increased by a command provided from the microprocessor 152 and the current programmed rate is stored in RAM 154 for periodic use by digital controller/timer circuit 158 in the drug delivery routine. Then, the analog memory address for the ATD signal for the voiced statement of the increased rate is applied by the microprocessor 152 on the data and control bus 150 to the analog storage/playback IC 200 to cause the emission of the voiced statement to confirm the rate change. At this point, assuming that the maximum rate has not been reached, the medical care provider can choose to increase the rate by the next rate increment by leaving the magnet 130 in place for a few seconds and by repeating the process. Or, the medical care provider can choose to terminate the programming sequence at the new programmed rate by simply removing the magnet 130 before the next rate change is voiced. A similar process is followed if it is desired to decrease the drug delivery rate by reversing the magnetic field and using the memory address "0F" to generate the descending scale musical tone or "Rate decreasing" voiced statement.

In this case of a configuration using the programming and interrogation system of FIG. 8, the patient 102 can also be provided with a magnet 130 and instructions to follow to increase or decrease a drug delivery therapy to treat pain, for example. In this case, it will be assumed that the IMD is programmed at manufacture with musical tones using the audible sound input 206 at addresses "00", "0A", "0D" rather than the equivalent voiced statements. The patient 102 is advised to apply the magnet 130 and to follow the above described routine until the ascending scale musical tone is heard. Then, the rate can be increased or decreased by following the steps described above. For safety reasons, the maximum rate that the patient can program may be limited in a manner described, for example, in commonly assigned U.S. Pat. No. 5,443,486 to Hrdlicka et al., incorporated herein by reference.

FIG. 12 is a chart depicting the memory address locations of ATD signals for emitting voiced statements or musical tones in interrogation and programming sequences of an implantable electrical stimulator 160h of FIG. 10 having an operating system of FIG. 8 or FIG. 9 or a hard wired equivalent thereto. Such implantable electrical stimulators include but are not limited to stimulators to electrically stimulate the spinal cord, peripheral nerves, muscles and muscle groups, the diaphragm, parts of the brain, body organs and the like with electrical pulses delivered to electrodes located at the desired site of stimulation.

Commercially available electrical stimulators of this type include the MEDTRONIC® Itrel II® electrical stimulator, Itrel III® electrical stimulator, and the Matrix® electrical stimulator, and a dual channel Itrel® electrical stimulator.

The chart of FIG. 12 depicts the memory addresses for ATD signals for emitting voiced statements or musical tones in an interrogation sequence of current IMD information at address locations "00"–"1D" and in a programming sequence of the programmable parameter values and modes at address locations "00"–"14" and "18"–"1D". The chart of FIG. 12 also shows the memory address locations "0E" and "1F" for emitting ascending scale and descending scale musical tones in a programming sequence for increasing or decreasing a stimulation parameter, e.g., pulse amplitude or pulse width or pulse rate or electrodes at address locations "00"–"14" and "18"–"1D". In the interrogation and programming sequences, the medical care provider can commence the interrogation using either a programmer in the case of a configuration using the operating system of FIG. 9 or a magnet 130 in the case of a configuration using the operating system of FIG. 8. The patient can be provided with a limited function programmer for programming one or more of the programmable parameter values and operating modes.

The following description assumes that a magnet programming and interrogation system is used and assuming that the IMD 100 of FIG. 1 is an electrical stimulator 160h with the lead 120 applied to a muscle other than the heart. The medical care provider applies the magnet 130 over the MAGFET 70 which produces either the N or S signal on line 72 or 74 of FIG. 8. The logic circuit 78 responds by providing an interrupt to the microprocessor 152 to commence the interrogation routine. The memory address "15" is provided on bus 150 to analog storage/playback IC 200 which emits the voiced statements identifying the IMD. Then, the interrogation routine sequentially selects the programmed one of the addresses "00"–"06" for the current pulse rate, "07"–"0E" for the current (I.e., previously programmed) pulse width, and "0F"–"14" for the current pulse amplitude. The interrogation continues with the selection of the address "16" or "17" for the battery condition, the address "18" or "19" for the cycle ON or OFF state, and the addresses "1A"–"1D" of the programmed electrode configuration. The ATD signals cause the emission of voiced statements in these cases. In the illustration of FIG. 1, these statements are emitted at a volume that is not audible to the patient 102 but can be heard by the medical care provider using the stethoscope 142 or a simple audio amplifier.

During the interrogation sequence, the battery voltage is monitored and the appropriate one of the addresses "16" or "17" are provided to the analog storage/playback IC 200 at the specified point in the sequence. The detection of the magnet 130 causes the microprocessor 152 to suspend the periodic emission of the battery depletion warning that would take place at other times if the battery 13 is depleted to the ERI voltage. However, it will be understood that during the normal operation, these voiced statement or musical tone warnings at address "16" are emitted at a volume that can be heard by the patient as described above.

At this point, the magnet 130 can be withdrawn to end the interrogation sequence or it can be left in place or rotated end to end to commence the programming sequence to increase or decrease any of the programmable parameters, i.e., the pulse rate, width, amplitude, the cycle state and the electrodes. The programming sequence commences with a rate increasing mode by providing the address "1E" to cause the emission of the "increasing value" voiced statement or the ascending scale musical tone. Then, within the time of a few seconds, the medical care giver can either leave the magnet 130 in place to continue in the increasing mode or reverse it end to end to cause the programming sequence to switch to a decreasing mode. A system of successive magnet placements and removals similar to that employed in the sequence illustrated in FIGS. 3A–3C can be employed to successively program each parameter value and operating mode.

Assuming that the stimulation pulse rate is being programmed to an increased pulse rate, after continued application of the magnet for a few seconds, the pulse rate is incrementally increased by a command provided from the microprocessor 152. The new current programmed pulse rate is stored in RAM 154 for periodic use by digital controller/timer circuit 158 in the stimulation delivery routine. Then, the address "1E" for the ATD signal for the voiced statement of the increased rate is applied by the microprocessor 152 on the data and control bus 150 to the analog storage/playback IC 200 to cause the emission of the voiced statement or ascending scale musical tone to confirm the rate change. At this point, assuming that the maximum pulse rate has not been reached, the medical care provider can choose to increase the pulse rate by the next rate increment by leaving the magnet 130 in place for a few seconds and by repeating the process. Or, the medical care provider can choose to terminate the programming sequence at the new programmed pulse rate by simply removing the magnet 130 before the next rate change is voiced. A similar process is followed if it is desired to decrease the drug delivery rate.

In this case of a configuration using the programming and interrogation system of FIG. 8, the patient 102 can also be provided with a magnet 130 and instructions to follow to increase or decrease a drug delivery therapy to treat pain, for example. In this case, it will be assumed that the IMD is programmed at manufacture with musical tones using the audible sound input 206 at analog memory addresses "1E", and "1F", rather than the equivalent voiced statements. The patient 102 is advised to apply the magnet 130 and to follow the above described routine until the ascending scale musical tone is heard. Then, the rate can be increased by leaving the magnet in place or decreased by reversing the polarity of the magnetic field and listening for the decreasing scale musical tone.

These embodiments of the present invention are described above in the context of a micro-computer based IMD operating system where the programming and interrogation sequences are governed by algorithms stored in ROM 156 and that cooperate with logic circuitry and registers in the digital controller/timer circuit 158. The algorithm takes the place of the timing control circuit 202 and the address generation circuit 204 and the interconnections therebetween and with the analog storage/playback IC 200 of FIG. 5. It will be understood that such a circuit of FIG. 5 could be employed in a micro-computer based operating system. Conversely, it will be understood that these embodiments can also be practiced in a hardware based system that does use the circuit of FIG. 5 to sequentially address the analog memory addresses in the sequences described above with reference to FIGS. 11 and 12 and in other sequences that can be devised using the therapy delivery and monitoring systems of FIG. 10.

The preceding specific embodiments are therefore to be understood as illustrative of the many ways in which the principles of the invention may be practiced. It is to be understood, therefore, that other expedients known to those of skill in the art or disclosed herein may be employed without departing from the invention or the scope of the appended claims.

In the following claims, means-plus-function clauses are intended to cover the structures described herein as performing the recited function and not only structural equivalents but also equivalent structures. For example, although a nail and a screw may not be structural equivalents in that a nail employs a cylindrical surface to secure wooden parts together, whereas a screw employs a helical surface, in the environment of fastening wooden parts, a nail and a screw are equivalent structures.

It is therefore to be understood, that within the scope of the appended claims, the invention may be practiced otherwise than as specifically described without actually departing from the spirit and scope of the present invention.

We claim:

1. A method of audibly communicating a change in operation of an implantable medical device implanted in a patient in an audio frequency range to the patient and/or a medical care provider to confirm the change in operation comprising the steps of:

providing a programming signal from a location outside the body of the patient to make a change in an operation of the implantable medical device;

receiving the programming signal by receiver means located within the implantable medical device;

effecting a change in the operation of the implantable medical device signified by the programming signal received by the receiver means; and emitting an audible sound from the implantable medical device that is transmitted through the patient's body and signifies the change made in the operation of the implantable medical device.

2. The method of claim 1, wherein said emitting step further comprises the steps of:

generating an audio transducer drive signal; and applying said audio transducer drive signal to an audio transducer located within said implantable device, thereby causing said audio transducer to emit an audible sound when driven by said audio transducer drive signal.

3. The method of claim 2, wherein said audible sound is a musical tone that signifies the change in the operation of the implantable medical device and said emitting step further comprises the steps of:

storing at least one audio transducer drive signal for application to said audio transducer correlated to a change in an operation of the implantable medical device at a memory address of memory within said implantable medical device;

generating the memory address of the audio transducer drive signal correlated with the change in response to a change in the operation of the implantable medical device; and retrieving and applying the audio transducer drive signal from said memory to said audio transducer in response to a memory address generated by said address generation means, whereby a musical tone accompanying the change in operation is emitted by said audio transducer means.

4. The method of claim 2, wherein said emitting step further comprises the steps of:

emitting a first musical tone that signifies an increase in an operating parameter of the implantable medical device in response to a programming signal for increasing the therapy parameter; and emitting a second musical tone that signifies a decrease in an operating parameter of the implantable medical device in response to a programming signal for decreasing the therapy parameter.

5. The method of claim 4, wherein said emitting step further comprises the steps of:

storing a first audio transducer drive signal for generating said first musical tone at a first memory address;

storing a second audio transducer drive signal for generating said second musical tone at a second memory address;

generating said first memory address of said first audio transducer drive signal in response to an increase in an operating parameter;

generating said second memory address of said second audio transducer drive signal in response to a decrease in an operating parameter;

in response to said first memory address, retrieving said first audio transducer drive signal from said memory and for applying the retrieved first audio transducer drive signal to said audio transducer to emit said first musical tone; and in response to said second memory address, retrieving said second audio transducer drive signal from said memory and applying the retrieved second audio transducer drive signal to said audio transducer to emit said second musical tone.

6. The method of claim 2, wherein said emitting step further comprises the steps of:

emitting an increase sequence of ascending scale musical tones that signifies an increase in an operating parameter of the implantable medical device in response to a programming signal for increasing the operating parameter; and emitting a decrease sequence of descending scale musical tones that signifies a decrease in an operating parameter of the implantable medical device in response to a programming signal for decreasing the operating parameter.

7. The method of claim 6, wherein said emitting step further comprises the steps of:

storing a first audio transducer drive signal for generating said increase sequence of ascending scale musical tones in memory at a first memory address;

storing a second audio transducer drive signal for generating said decrease sequence of ascending scale musical tones in memory at a second memory address;

generating said first memory address of said first audio transducer drive signal in response to an increase in an operating parameter;

generating said second memory address of said second audio transducer drive signal in response to a decrease in an operating parameter;

in response to said first memory address, retrieving said first audio transducer drive signal from said memory and applying the retrieved first audio transducer drive signal to said audio transducer to emit said increase sequence of ascending scale musical tones; and in response to said second memory address, retrieving said second audio transducer drive signal from said memory and applying the retrieved second audio transducer drive signal to said audio transducer to emit said decrease sequence of ascending scale musical tones.

8. The method of claim 2, wherein said audible sound comprises a voiced statement in a human language that states the change in the operation of the implantable medical device, and said emitting step further comprises:

storing in memory at least one audio transducer drive signal at a memory address correlated to at least one change in an operation of the implantable medical device;

in response to a change in the operation of the implantable medical device, generating the memory address of the audio transducer drive signal correlated with the change; and in response to a memory address generated in response to a change in the operation of the implantable medical device, retrieving and applying the audio transducer drive signal from said memory to said audio transducer, whereby a voiced statement accompanying the change in operation is emitted by said audio transducer means.

9. The method of claim 2, wherein said audible sound comprises a plurality of voiced statements in a human language that each state a change in the operation of the implantable medical device, and said emitting step further comprises:

storing in memory a plurality of audio transducer drive signals each at a memory address correlated to a change in an operation of the implantable medical device;

in response to a change in the operation of the implantable medical device, generating the memory address of the audio transducer drive signal correlated with the change; and in response to a generated memory address, retrieving and applying the audio transducer drive signal from said memory to said audio transducer, whereby a voiced statement accompanying the change in operation is emitted by said audio transducer means.

10. The method of claim 2, wherein said emitting step further comprises the steps of:

emitting a first voiced statement in a local human language that states an increase in an operating parameter of the implantable medical device; and emitting a second voiced statement in a local human language that states a decrease in an operating parameter of the implantable medical device.

11. The method of claim 10, wherein the step of emitting a first voiced statement includes selecting a local human language, and the step of emitting a second voiced statement includes selecting a local human language.

12. The method of claim 10, wherein said emitting step further comprises the steps of:

storing a first audio transducer drive signal for generating said first voiced statement in memory at a first memory address;

storing a second audio transducer drive signal for generating said second voiced statement in memory at a second memory address;

generating said first memory address of said first audio transducer drive signal in response to an increase in an operating parameter;

generating said second memory address of said second audio transducer drive signal in response to a decrease in an operating parameter;

in response to said first memory address, retrieving said first audio transducer drive signal from said memory and applying the retrieved first audio transducer drive signal to said audio transducer to emit said first voiced statement; and in response to said second memory address, retrieving said second audio transducer drive signal from said memory and applying the retrieved second audio transducer drive signal to said audio transducer to emit said second voiced statement.

13. The method of claim 1, wherein the implantable medical device is a therapy delivery device and the operation or change in operation is the delivery of a therapy or a change in a therapy delivered to the patient that is initiated by the patient and/or medical care provider.

14. A system for audibly communicating a change in operation of an implantable medical device implanted in a patient in an audio frequency range to the patient and/or a medical care provider to confirm the change in operation comprising:

means for providing a programming signal from a location outside the body of the patient to make a change in an operation of the implantable medical device;

means for receiving the programming signal by receiver means located within the implantable medical device;

means for effecting a change in the operation of the implantable medical device signified by the programming signal received by the receiver means; and sound emitting means for emitting an audible sound from the implantable medical device that is transmitted through the patient's body and signifies the change made in the operation of the implantable medical device.

15. The system of claim 14, wherein said sound emitting means further comprises:

means for generating an audio transducer drive signal; and means for applying said audio transducer drive signal to an audio transducer located within said implantable device, thereby causing said audio transducer to emit an audible sound when driven by said audio transducer drive signal.

16. In conjunction with an implantable medical device, a system for emitting audible sounds from the implantable medical device implanted in a patient that may be heard by the patient and/or a medical care provider to confirm a change in an operation of the implantable medical device comprising:

means located outside the body of the patient and selectively operable by a medical care provider and/or the patient for providing a programming signal to the implantable medical device to make a change in an operation of the implantable medical device;

receiver means located within the implantable medical device for receiving the programming signal;

operation control means located within said implantable medical device for controlling an operation thereof and responsive to the received programming signal for making a change in the operation of the implantable medical device signified by the programming signal;

audio transducer means located within said implantable device for emitting an audible sound when driven by an audio transducer drive signal; and audio feedback means located within said implantable medical device and responsive to said operation control means for generating an audio transducer drive signal and applying the audio transducer drive signal to said audio transducer, thereby causing said audio transducer to emit an audible sound signifying that a change has been made in the operation of the implantable medical device.

17. The system of claim 16, wherein said audible sound is a musical tone that signifies the change in the operation of the implantable medical device.

18. The system of claim 17, wherein said audio feedback means further comprises:

storage means for storing at least one audio transducer drive signal for application to said audio transducer correlated to a change in an operation of the implantable medical device at a memory address;

address generation means responsive to a change in the operation of the implantable medical device for generating the memory address of the audio transducer drive signal correlated with the change; and retrieval means responsive to a memory address generated by said address generation means for retrieving and applying the audio transducer drive signal from said storage means to said audio transducer, whereby a musical tone accompanying the change in operation is emitted by said audio transducer means.

19. The system of claim 16, wherein said audible sounds include a first musical tone that signifies an increase in an operating parameter of the implantable medical device in response to a programming signal for increasing the operating parameter and a second musical tone that signifies a decrease in the operating parameter of the implantable medical device in response to a programming signal for decreasing the operating parameter.

20. The system of claim 19, wherein said audio feedback means further comprises:

storage means for storing a first audio transducer drive signal for generating said first musical tone at a first memory address and a second audio transducer drive signal for generating said second musical tone at a second memory address;

address generation means responsive to an increase in an operating parameter for generating said first memory address of said first audio transducer drive signal and responsive to a decrease in an operating parameter for generating said second memory address of said second audio transducer drive signal; and retrieval means responsive to said first memory address generated by said address generation means for retrieving said first audio transducer drive signal from said storage means and for applying the retrieved first audio transducer drive signal to said audio transducer to emit said first musical tone and responsive to said second memory address generated by said address generation means for retrieving said second audio transducer drive signal from said storage means and for applying the retrieved second audio transducer drive signal to said audio transducer to emit said second musical tone.

21. The system of claim 16, wherein said audible sounds include an increase sequence of ascending scale musical tones that signifies an incremental increase in an operating parameter of the implantable medical device in response to a programming signal for increasing the operating parameter and a decrease sequence of descending scale musical tones that signifies an incremental decrease in the operating parameter of the implantable medical device in response to a programming signal for decreasing the operating parameter.

22. The system of claim 21, wherein said audio feedback means further comprises:

storage means for storing a first audio transducer drive signal for generating said increase sequence of ascending scale musical tones at a first memory address and a second audio transducer drive signal for generating said decrease sequence of descending scale musical tones at a second memory address;

address generation means responsive to an increase in an operating parameter for generating said first memory address of said first audio transducer drive signal and responsive to a decrease in an operating parameter for generating said second memory address of said second audio transducer drive signal; and retrieval means responsive to said first memory address generated by said address generation means for retrieving said first audio transducer drive signal from said storage means and for applying the retrieved first audio transducer drive signal to said audio transducer to emit said ascending scale musical tones accompanying an incremental increase in an operating parameter of the implantable medical device in response to a programming signal and responsive to said second memory address generated by said address generation means for retrieving said second audio transducer drive signal from said storage means and for applying the retrieved second audio transducer drive signal to said audio transducer to emit said descending scale musical tones accompanying an incremental decrease in an operating parameter of the implantable medical device in response to a programming signal.

23. The system of claim 16, wherein said audible sound comprises a voiced statement in a local human language that states the change in the operation of the implantable medical device, and said audio feedback means further comprises:

storage means for storing at least one audio transducer drive signal at a memory address correlated to at least one change in an operation of the implantable medical device;

address generation means responsive to a change in the operation of the implantable medical device for generating the memory address of the audio transducer drive signal correlated with the change; and retrieval means responsive to a memory address generated by said address generation means for retrieving and applying the audio transducer drive signal from said storage means to said audio transducer, whereby a voiced statement accompanying the change in operation is emitted by said audio transducer means.

24. The system of claim 23, wherein the local human language comprises a user selectable local human language.

25. The system of claim 16, wherein said audible sound comprises a plurality of voiced statements in a human language that each state a change in the operation of the implantable medical device, and said audio feedback means further comprises:

storage means for storing a plurality of audio transducer drive signals each at a memory address correlated to a change in an operation of the implantable medical device;

address generation means responsive to a change in the operation of the implantable medical device for generating the memory address of the audio transducer drive signal correlated with the change; and retrieval means responsive to a memory address generated by said address generation means for retrieving and applying the audio transducer drive signal from said storage means to said audio transducer, whereby a voiced statement accompanying the change in operation is emitted by said audio transducer means.

26. The system of claim 25, wherein the local human language comprises a user selectable local human language.

27. The system of claim 16, wherein said audible sound comprises a first voiced statement in a local human language that states an increase in an operating parameter of the implantable medical device and a second voiced statement in a human language that states a decrease in an operating parameter of the implantable medical device, and said audio feedback means further comprises:

storage means for storing a first audio transducer drive signal at a first memory address correlated to an increase in an operating parameter of the implantable medical device and a second audio transducer drive signal at a second memory address correlated to a decrease in an operating parameter of the implantable medical device;

address generation means responsive to an increase in an operating parameter of the implantable medical device for generating said first memory address and responsive to a decrease in an operating parameter of the implantable medical device for generating said second memory address; and retrieval means responsive to said first memory address generated by said address generation means for retrieving said first audio transducer drive signal from said storage means and for applying the retrieved first audio transducer drive signal to said audio transducer to emit said first voiced statement accompanying an incremental increase in an operating parameter of the implantable medical device in response to a programming signal and responsive to said second memory address generated by said address generation means for retrieving said second audio transducer drive signal from said storage means and for applying the retrieved second audio transducer drive signal to said audio transducer to emit said second voiced statement accompanying an incremental decrease in an operating parameter of the implantable medical device in response to a programming signal.

28. The system of claim 26, wherein the local human language comprises a user selectable local human language.

29. The system of claim 16, wherein the implantable medical device is a therapy delivery device and the change in operation or in an operating parameter is the delivery of a therapy or a change in a therapy delivered to the patient initiated by the patient and/or the medical care provider.

* * * * *